(12) United States Patent
Caricasole et al.

(10) Patent No.: US 6,593,121 B1
(45) Date of Patent: Jul. 15, 2003

(54) HUMAN DIACYLGLYCEROL KINASE β (HDAGKβ) PROTEIN AND NUCLEOTIDE SEQUENCES ENCODING THE SAME

(75) Inventors: Andrea Caricasole, Rome (IT); Fabrizio Caldara, Verona (IT); Cinzia Felicita Sala, Verona (IT)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/913,301

(22) PCT Filed: Dec. 23, 1999

(86) PCT No.: PCT/GB99/04421

§ 371 (c)(1),
(2), (4) Date: Sep. 13, 2001

(87) PCT Pub. No.: WO00/47723

PCT Pub. Date: Aug. 17, 2000

(30) Foreign Application Priority Data

Feb. 15, 1999 (GB) ................................................ 9903430

(51) Int. Cl.[7] .............................. C12N 9/12; C12Q 1/48
(52) U.S. Cl. ........................................... 435/194; 435/15
(58) Field of Search .................................... 435/194, 15

(56) References Cited

PUBLICATIONS

Goto, K and Kondo, H. Molecular cloning and expression of a 90–kDa diacylglycerol kinase that predominantly localizes in neurons. Proc Natl Acad Sci U S A. Aug. 15, 1993;90(16):7598–602. EMBL AccNo. BAA03675. Alignment with SEQ ID NO: 4.*
Kai M, et al, Molecular cloning of a diacylglycerol kinase isozyme . . . J Biol Chem. Jul. 15, 1994;269(28):18492–8. EMBL AccNo. BAA03675. Alignment with SEQ ID No:4.*
Goto K. et al. Cloning and expression of a cytoskeleton–associated diacyglycerol kinase . . . Proc Natl Acad Sci U S A. Dec. 20, 1994;91(26):13042–6. EMBL AccNo. BAA07480.1. Alignment with SEQ ID No.:4.*

Fujikawa et al., "Isolation and Characterization of the human diacylglycerol kinase gene", *The Biochemical Journal* 294:2 443–449 (Sep. 1993).
Goddat et al., "Derivatives of Di–O–octanoylglycerol and Mono–O–octylglycerol as modulators of protein kinase C and diacylglycerol kinase activities", LIPIDS 27: 5 331–338 (May 1992).
Goto et al., "Molecular cloning and expression of a 90–kDa diacylglycerol kinase that predominantly localizes in neurons", *Proc. Natl. Acad. Sci. USA* 90:16 7598–7602 (Aug. 1993).
Houssa et al. "Cloning of a novel human diacylglycerol kinase (DGK theta) containing three cystein–rich domains, a proline–rich region, and a pleckstrin homology domain with an overlapping ras–associating domain", *The Journal of Biological Chemistry* 272:16 10422–10428 (Apr. 1997).
Nagase et al., "Prediction of the coding sequences of unidentified human genes. XI. The complete sequences of 100 new cDNA clones from brain which code for large proteins in vitro", *DNA Research* 5:277–286 (1998).
Nobe et al., "Activation of diacylglycerol kinase by carbacho 1 in guinea pig taenia coli", *Biochemical Pharmacology* 48:11 2205–2014 (Nov. 1994).
Nobe et al., "Alternations of diacylglycerolkinase in streptozotocin–induced diabetic rats", *Cellular Signalling* 10:7 465–471 (Jul. 1998).
Sakane et al., "Molecules in focus: Diacylglycerol kinase", *International Journal of Biochemistry & Cell Biology* 29:10 1139–1143 (Oct. 1997).

* cited by examiner

*Primary Examiner*—Rebecca E. Prouty
*Assistant Examiner*—Sheridan L. Swope
(74) *Attorney, Agent, or Firm*—Virginia C. Bennett

(57) ABSTRACT

The present invention relates to human diacylglycerol kinase proteins (hDAGK) and particularly to human diacylglycerol kinase β (hDAGKβ) protein, and to related nucleotide sequences, expression vectors, cell lines, antibodies, screening methods, compounds, methods of production and methods of treatment, as well as other related aspects.

3 Claims, 4 Drawing Sheets

US 6,593,121 B1

HUMAN DIACYLGLYCEROL KINASE β (HDAGKβ) PROTEIN AND NUCLEOTIDE SEQUENCES ENCODING THE SAME

This application is filed pursuant to 35 U.S.C. §371 as a United States National Phase Application of International Application No. PCT/GB99/04421 filed Dec. 23, 1999, which claims priority from GB9903430.8 filed Feb. 15, 1999.

FIELD OF THE INVENTION

The present invention relates to human diacylglycerol kinase proteins (hDAGK) and particularly to human diacylglycerol kinase β (hDAGKβ) protein, and to related nucleotide sequences, expression vectors, cell lines, antibodies, screening methods, compounds, methods of production and methods of treatment, as well as other related aspects.

BACKGROUND OF THE INVENTION

Diacylglycerol kinases (DAGKs) are a family of enzymes that convert diacylglycerol (DAG) to phosphatidic acid and are therefore known to attenuate DAG-dependent protein kinase C activation (PCK) (1).

Five types of DAGKs have been described. Type I DAGKs contains four conserved regions, the N-terminal region (C 1), two sets of EF-hand motifs (C2), two cysteine-rich zinc finger like structures (C3) and the C-terminal region (C4). Type II isoenzymes contain a pleckstrin homology (PH) domain at the N-terminus. Type Ill contains only the zinc finger (C3) and the catalytic region (C4). Type IV contains four ankyrin repeats near the carboxyl terminus. Type V contains three instead of two zinc finger structures, a proline-rich region and a PH domain with an overlapping Ras-associating (RA) domain. All share two domains, the C2 and the C3 (2).

A 90 kDa DAGKβ (3) belonging to type I was found by screening a rat brain cDNA library using fragments of rat a DAGK cDNA under low stringency conditions. The cDNA clone obtained was completely sequenced. The rat DAGKβ cDNA has an open reading frame of 5927 nucleotides and encodes for a protein of 801 amino acids with a predicted relative molecular mass of 90,000. Analysis of the amino acid sequence identified 2 EF-hand motifs (aa 152–180 and 197–225), of two cysteine-rich zinc-finger-like sequences (aa 257–292 and 319–356), and putative ATP-binding sites (aa 266–294 and 533–560).

Brain expression has been described for the known DAGK isoforms (2), which include DAGKα, DAGKη, DAGKζ and DAGKθ. A particular distribution restricted to specific regions of the central nervous system (CNS) was described for the DAGKβ form, originally identified in the rat (90 Da DAGKβ). The rat beta form is predominantly localised in neurons of the caudate-putamen, the accubens nucleus and the olfactory tubercle. Such brain regions are among the main CNS dopaminergic, serotonergic, acetylcholinergic and glutamatergic terminal fields (4).

It has also been demonstrated that some metabotropic dopamine, serotonin, glutamate, acetylcholine and several peptide receptors are coupled with the phosphoinositide signal transduction system (5). Lithium is known as one of the most effective therapies for bipolar disorders. Although the biological mechanisms of the mood stabilising properties of lithium are not well understood, experimental evidence indicates that lithium modulates the phosphoinositide signal transduction system (6) by inhibiting the phosphatase that liberates inositol from inositol phosphate (IP), and by modifying the activity of the phospholipase C (PLC)-dependent signalling pathways, including the levels of the second messenger diacylglycerol (DAG) that activates protein kinase C (PKC).

With this background in mind, the present inventors have determined that the DAGKs, and particularly the human ortholog of rat 90 kDa DAGKβ (hDAGKβ) and variants thereof will provide targets for the development of novel mood stabilising agents and therapeutic agents for treatment of other disorders.

Clearly there is a need for proteins and related nucleotide sequences that may be used to screen for mood stabilising agents and which may also play a role in preventing, ameliorating or correcting mood disorders and dysfunction and other neurological diseases.

Accordingly, it is an object of the present invention to identify targets for screening of novel therapeutic agents. It is another object of the invention to locate and characterise human DAGKβ and variants thereof. Other objects of the present invention will become apparent from the following detailed description thereof.

SUMMARY OF THE INVENTION

According to one embodiment of the present invention there is provided an isolated human diacylglycerol kinase β (hDAGKβ) protein or a variant thereof. In a particularly preferred embodiment of this invention the human diacylglycerol kinase β (hDAGKβ) has the amino acid sequence set out in Seq ID No 1 or Seq ID No 4. The hDAGKβ protein having the amino acid sequence set out in Seq ID No 4 is referred to as SV-hDAGKβ protein.

According to one embodiment of the present invention there is provided a nucleotide sequence encoding a human diacylglycerol kinase β (hDAGKβ) protein or a variant thereof, or a nucleotide sequence that is complementary thereto. In a particular preferred embodiment of the invention the polynucleotide comprises the sequence set out in Seq ID No 3 or Seq ID No 6. The hDAGKβ protein having the polinucletide sequence set out in Seq ID No 6 is referred to as SV-hDAGKβ protein.

In accordance with another aspect of the invention there is provided an expression vector comprising a nucleic acid sequence as referred to above which is capable of expressing a hDAGKβ protein.

According to a further aspect of the invention there is provided a stable cell line comprising an expression vector as referred to above. Preferably the cell line is a modified HEK293T, CHO, HeLa, Sf9 or COS cell line.

According to yet a further aspect of the invention there is provided an antibody specific for a hDAGKβ protein.

According to still another aspect of the invention there is provided a method for identification of a compound that exhibits DAGK modulating activity, comprising contacting a DAGK protein with a test compound and detecting modulation of enzyme activity or detecting enzyme inactivity. Preferably the DAGK is hDAGKβ or a variant thereof.

According to another aspect of the invention there is provided a compound which modulates hDAGK activity, identifiable by the method referred to above. Preferred compounds according to the present invention are those that modulate hDAGKβ activity or a variant thereof.

According to another aspect of the invention there is provided a compound that modulates hDAGK activity. Preferred compounds according to the present invention are those that modulate hDAGKβ activity or a variant thereof.

According to a further aspect of the invention there is provided a method of treatment or prophylaxis of a disorder that is responsive to modulation of hDAGK activity in a human patient, which comprises administering to said patient an effective amount of a compound as referred to above. Conveniently the hDAGK is hDAGKβ or a variant thereof. Preferably the disorder is a mood disorder, epilepsy, a neurodegenerative disorder, anxiety, schizophrenia, migraine, drug dependence, stroke, Alzheimer's dementia or Parkinson's disease.

According to a further aspect of the invention there is provided a method of treatment or prophylaxis of a disorder that is responsive to modulation of hDAGK activity in a human patient which comprises administering to said patient an effective amount of a modulator of hDAGK activity. Conveniently the hDAGK is hDAGKβ or a variant thereof. Preferably the disorder is a mood disorder, epilepsy, a neurodegenerative disorder, anxiety, schizophrenia, migraine, drug dependence, stroke, Alzheimer's dementia or Parkinson's disease.

According to another aspect of the invention there is provided use of a compound as referred to above in a method of formulating a medicament for treatment or prophylaxis of a disorder that is responsive to modulation of hDAGK activity in a human patient. Conveniently the hDAGK is hDAGKβ or a variant thereof. Preferably the disorder is a mood disorder, epilepsy, a neurodegenerative disorder, anxiety, schizophrenia, migraine, drug dependence, stroke, Alzheimer's dementia or Parkinson's disease.

According to another aspect of the invention there is provided use of a modulator of hDAGK activity in a method of formulating a medicament for treatment or prophylaxis of a disorder that is responsive to modulation of hDAGK activity in a human patient. Conveniently the hDAGK is hDAGKβ or a variant thereof. Preferably the disorder is a mood disorder, epilepsy, a neurodegenerative disorder, anxiety, schizophrenia, migraine, drug dependence, stroke, Alzheimer's dementia or Parkinson's disease.

According to another aspect of the invention there is provided a method of producing a hDAGKβ protein or a variant thereof comprising introducing into an appropriate cell line a suitable vector comprising a nucleotide sequence encoding for a hDAGKβ protein or a variant thereof, under conditions suitable for obtaining expression of the hDAGKβ protein or variant.

Seq ID No 3 shows the complete nucleotide sequence of the human DAGKβ. Seq ID No 5 shows the complete nucleotide sequence of the SV-hDAGKβ.

Seq ID No 1 shows the nucleotide and encoded amino acid sequence of the human DAGKβ sequence. Seq ID No 4 shows the nucleotide and encoded amino acid sequence of the SV-hDAGKβ.

Seq ID No 7 shows pairwise alignment of hDAGKβ and SV-hDAGKβ full-length amino acids sequences with rat homologue.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1A:
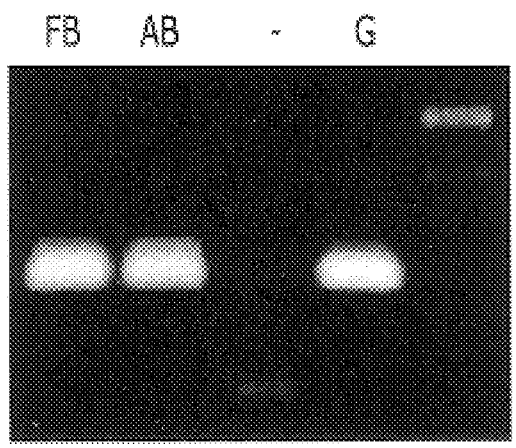
FIGS. 1A and 1B shows a reverse transcriptase polymerase chain reaction (RT-PCR) of human adult and human foetal brain (polyA+RNA).

Throughout the present specification and the accompanying claims the words "comprise" and "include" and variations such as "comprises", "comprising", "includes" and "including" are to be interpreted inclusively. That is, these words are intended to convey the possible inclusion of other elements or integers not specifically recited, where the context allows.

As referred to above, the present invention relates to human diacylglycerol kinase β (hDAGKβ) protein, sequence information for which is provided in Seq ID No 1 or Seq ID No 4. In the context of this invention the term "isolated" is intended to convey that the protein is not in its native state, insofar as it has been purified at least to some extent or has been synthetically produced, for example by recombinant methods. The term "isolated" therefore includes the possibility of the protein being in combination with other biological or non-biological material, such as cells, suspensions of cells or cell fragments, proteins, peptides, organic or inorganic solvents, or other materials where appropriate, but excludes the situation where the protein is in a state as found in nature.

Routine methods can be employed to purify and/or synthesise the proteins according to the invention. Such methods are well understood by persons skilled in the art, and include techniques such as those disclosed in Sambrook et al. (7), the disclosure of which is included herein in its entirety by way of reference.

By the term "variant" what is meant throughout the specification and claims is that other peptides or proteins which retain the same essential character of the diacylglycerol kinase for which sequence information is provided, are also intended to be included within the scope of the invention. For example, other peptides or proteins with greater than about 80%, preferably at least 90% and particularly preferably at least 95% homology with the sequences provided are considered as variants of the enzymes. Such variants may include the deletion, modification or addition of single amino acids or groups of amino acids within the protein sequence, as long as the peptide maintains the biological functionality of a hDAGKβ. The rat DAGKβ protein is of course excluded from the definition of "variant".

Human DAGKβ is expressed in human brain and has the highest (~95% identity) sequence homology with the rat DAGKβ. Therefore, hDAGKβ is likely to be the human orthologue of rat DAGKβ. Seq ID No 1 reveals a 3926 bp (base pair) open reading frame which encodes an 804 amino acid protein. This deduced protein sequence is ~95% identical to the rat DAGKβ and shares many of its characteristics and all the domains.

The invention also includes nucleotide sequences identified as Seq ID No 1 or Seq ID No 4 that encode for hDAGKβ protein or variants thereof as well as nucleotide sequences that are complementary thereto. Preferably the nucleotide sequence is a DNA sequence and most preferably, a cDNA sequence. Such nucleotides can be isolated or synthesised according to methods well know in Sambrook et al. (7), the disclosure of which is included herein in its entirety by way of reference.

The present invention also includes expression vectors that comprise nucleotide sequences encoding for the hDAGKβ protein or variants thereof. A further aspect of the invention relates to an expression vector comprising nucleotide sequences encoding for hDAGKβ protein or variants thereof. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Suitable vectors would be apparent to persons skilled in the art. By way of further example in this regard we refer to (7), the disclosure of which is included herein in its entirety.

The invention also includes cell lines that have been modified to express the novel protein and variants thereof. Such cell lines include transient, or preferably stable higher eukaryotic cell lines, such as mammalian cells or insect cells, lower eukaryotic cells, such as yeast or prokaryotic cells such as bacterial cells. Particular. examples of cells that have been modified by insertion of vectors encoding for the proteins according to the invention include the mammalian HEK293T, CHO, HeLa, Sf9 and COS cells.

It is also possible for the protein and variants thereof of the invention to be transiently expressed in a cell line, such as for example in a baculovirus expression or in an *E. coli* system. Such systems, which are adapted to express the proteins according to the invention, are also included within the scope of the present invention.

According to another aspect, the present invention relates to antibodies (either polyclonal or preferably monoclonal antibodies) which have been raised by standard techniques and are specific for the protein or variants thereof according to the invention. Such antibodies could for example, be useful in purification, isolation or screening involving immuno-precipitation techniques and may be used as tools to further elucidate protein function, or indeed as therapeutic agents in their own right. Antibodies may also be raised against specific epitopes of the proteins according to the invention.

An important aspect of the present invention is the use of hDAGK proteins in screening methods designed to identify compounds which act as enzyme ligands and which may be useful as modulators of enzymatic activity. In general terms, such screening methods will involve contacting the hDAGK protein concerned, which may be any known or as yet unrecognised hDAGK protein or variant thereof, preferably hDAGKβ, with a test compound and then detecting modulation of the enzymatic activity, or indeed detecting enzyme inactivity, which results.

The present invention also includes within its scope those compounds, which are identified as possessing useful hDAGK modulation activity. Such activity can be determined by the screening methods referred to above. The screening methods comprehended by the invention are generally well known to those skilled in the art. An example of such an approach is provided in the experimental section of this specification.

Another aspect of the present invention is the use of compounds which have been identified by screening techniques referred to above, or other compounds found to exhibit hDAGK modulating activity, in the treatment or prophylaxis of disorders that are responsive to modulation of a hDAGK activity, particularly hDAGKβ activity, in a human patient. By the term "modulation" what is meant is that there will be either agonism or antagonism of the enzymatic activity, which results from ligand binding of the compound at the catalytic or regulatory sites of the hDAGK protein. These proteins have been implicated in disorders of the central nervous system (CNS), and therefore, modulation of hDAGK enzymatic activity in these tissues will result in a positive therapeutic outcome in relation to such disorders.

In particular, the compounds which will be identified using the screening techniques according to the invention will have utility for treatment and/or prophylaxis of disorders such as mood disorders, epilepsy, anxiety, schizophrenia, drug dependence, neurodegenerative disorders. Some specific examples of disorders which may be treated or prevented by administration of compounds identified in the screening techniques according to the present invention are unipolar and bipolar depression, stroke, Alzheimer's dementia, Parkinson's disease, smoking cessation, and ethanol, nicotine, cocaine and heroine abuse. It is to be understood, however, that the mention of such disorders is by way of example only, and is not intended to be limiting on the scope of the invention.

The compounds which are identified according to the screening methods outlined above may be formulated with standard pharmaceutically acceptable carriers and/or excipients, as is routine in the pharmaceutical art, and as is fully described in Remmington's Pharmaceutical Sciences, Mack Publishing Company, Eastern Pa., 17th Ed, 1985; the disclosure of which is included herein in its entirety by way of reference.

The compounds may be administered via enteral or parenteral routes such as via oral, buccal, anal, pulmonary, intravenous, intraarterial, intramuscular, intraperitoneal, topical or other appropriate administration routes.

It will further be appreciated that the amount of a compound of the invention required for use in treatment will vary with the nature of the condition being treated, the route of administration and the age, sex, weight and general condition of the patient, and will ultimately be at the discretion of the attendant physician. In general, however, doses employed for adult human treatment will typically be in the range of between about 2 mg to about 800 mg per day.

The present invention will be further explained, by way of example, in the following experimental section.

Experimental
Identification of Human Genomic Sequences Corresponding to Bipolar Patients' ESTs Obtained by in Silico Analysis An extensive search using keywords in both public (GenBank) and private (Incyte) databases resulted in some ESTs annotated as specific for bipolar diseases. Most of GenBank ESTs referred to the Stanley Neurovirology Laboratory (John Hopkins School of Medicine, Baltimore), where they were obtained by subtractive hybridisation of frontal cortex RNA from individuals with bipolar disorder and individuals without psychiatric diseases as controls.

A first comparison against dbEST (8) using the Blastn (9) alignment program revealed that most of the bipolar specific ESTs do not correspond to any sequence of known function and no other overlapping ESTs can be found to create contigs and enlarge the sequences. Therefore, in a preliminary analysis only those presenting enough information to proceed with an in silico work were considered, in particular those ESTs that showed 100% identity with a genomic sequence. The genomic sequence identified for the EST-S4 (GenBank acc. n. AF019352) is an unannotated 172-Kb length sequence (GenBank acc. n. AC005039) consisting of 2 contigs, for which the order is not known, interrupted by an N bases gap.

A detailed analysis was performed on the whole uncharacterised region with the aim of extracting all the high complexity sub-regions that usually contain coding sequences. The low complexity and highly redundant regions found in portions of the sequence were isolated using the SEG (segment sequences by local complexity) tool (10, 11,) and compared against all the available sequence databases to exclude any possible translation. As expected, these low complexity regions corresponded mainly to different families of ALU sequences therefore were masked in the subsequent gene prediction approach.

The EST-S4 Belongs to a Novel Human Gene Orthologue to the Rat DAGKβ gene

The Blastx alignment program was used to compare the 4 Kb genomic region surrounding the EST-S4 region with the amino acid sequences of SwissProt and TREMBL databases. Only some local similarities with a high statistical significance with the rat DAGKβ gene were evidenced and suggest an authentic relationship. To verify if this result was consistent with a possible gene construct an in silico exon trapping method (12) was applied on the AC005039 sequence. GeneMark (13), Xpound (12) and GRAIL (14) exon prediction tools were used to locate the potential coding regions within AC005039. Three exons (a, b and c) were found to be consistent with the same ORF and to correspond to exons 22, 23 and 24 of the rat DAGKβ gene. The region was 32 Kb wide and contained the EST-S4 sequence.

Searching the more recent set of public domain nucleotide sequences (New GenBank updates), a partial mRNA sequence of 3742 bp from a human adult brain (KIAA0718, Acc. No. AB018261) was found to partially overlap the 4 kb genomic sequence (100% identity with the three exons so far identified). The predicted protein sequence (defined in GenPept as KIAA0718 protein) was limited to 742 aa with a N-terminal truncation described. Homology search in protein databases indicates a high similarity with rat DAGKβ.

Chromosomal Localisation of the Putative hDAGKβ

The genomic sequence AC005039 is annotated as an unfinished sequence mapped on chromosome 7. An "In silico" STS (Sequence Tagged Site) content analysis (15) was performed on the sequence, and the 3 STSs (sWSS2950, D7S2174 and sWSS2190) found in the sequence confirmed that the hDAGKβ is localised on 7p21.

In silico Cloning of Full-length of the hDAGKβ mRNA

Figure 1B:
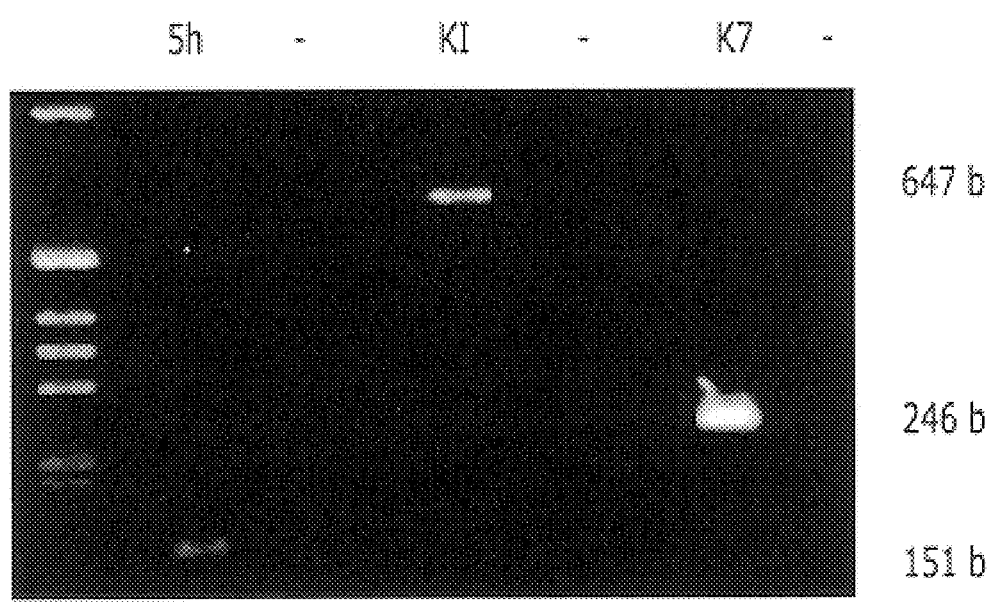

Comparing (tBlastn) the first two exons of the rat protein against the GenBank HTG (high throughput genomic) sequences database, two further overlapping genomic sequences (100% identity) were identified (GenBank acc. n. H_GS120K9 and AC006045). These sequences do not overlap with AC005039 but both contain four STSs (sWSS3226, sWSS822, sWSS2758, and sWSS2091) and belong to the same YAC clone (CEPH791G01) where AC005039 is located. These data indicate that the exons identified belong to the hDAGKβ gene and provide the information missing in the KIAA0718 structure to complete the full length sequence of the predicted protein Identification and Characterisation of Human DAGKβ Variants in cDNA Libraries Three DNA probes were used to screen a human foetal brain cDNA library (cat. n. 936206 Stratagene, La Jolla, Calif.). The 246 bp fragment was obtained by reverse transcriptase polymerase chain reaction (RT-PCR) (16) with the oligo pairs previously described (see above paragraph), and used for radioactive hybridisation. The two primer pairs DAGKIAAfor/DAGKIAArev (5'TGAAGACATTCCTGGAAGCC, 5'GACTGTGTACTTGCAGAAGG), and 5hDAGKfor/ 5hDAGKrev (5'CCATGACAAACCAGGAAAAATGG, 5'GATTATACTTTGCAAGCACACC) were used to obtain 2 RT-PCR products of 647 bp and of 151 bp respectively from foetal brain polyA+RNA (Clontech) (FIG. 1, panel B). The PCR conditions included an initial hot-start at 94° C. for 2 minutes, followed by 35 cycles at 94° C. for 1 minute, 56° C. (DAGKIAAfor/DAGKIAArev) or 58° C. (5hDAGKfor/ 5hDAGKrev) for 1 minute, 72° C. for 1 minute and terminated by 7 minutes at 72° C. The resulting PCR amplicons were separated on a 2% agarose gel and used for radioactive hybridisation.

To fully sequence the cDNA clones isolated, the library inserts were first subcloned in pBluescript KS vector (Stratagene, La Jolla, Calif.). After transformation, colonies were screened by hybridisation with the previously described probes. Positive colonies were subjected to direct sequencing (17) using the T3 and T7 primers. The DNA sequences obtained were assembled using the GCG package, translated and aligned with the rat DAGKβ gene using CLUSTAL (18). Two positive clones were isolated using a human DAGKβ-specific probe covering sequences from position 1524 to position 2360 and their sequence covered by sequencing on both DNA strands. The clones contained the last three exons and part of the 3' untranslated region (UTR) of the hDAGKβ sequence.

The tissue distribution of hDAGKβ gene was established by radioactive hybridisation on multi-Tissue northern blots (Clontech) according to the manufacturer's recommendations. The probes were obtained by RT-PCR amplification of different portions of the coding region of hDAGKβ including the 3' splice variant specific probe.

Identification, Characterisation and Cloning of the 3' End of SV-DAGKβ Splice Variant The GCG package (Wisconsin Package Version 9.0, Genetics Computer Group (GCG), Madison, Wis.) was used to align the human genomic sequence surrounding the EST-S4 with the rat 90 kDa DAGKβ mRNA. The EST-S4 is located in the 30 Kb intron between exons b and c. It overlaps with the AC005039 genomic sequence 91 bp downstream the last amino acid of exon b. The genomic sequence contains two in frame stop codons and a possible polyadenylation signal is present on the EST sequence.

In order to verify if EST-S4 identifies a splice variant of the human DAGKβ gene, a reverse transcriptase polymerase chain reaction (RT-PCR) using the following primer pair: DAGK7for (5'TGCCMTGCAAATTGATGGG) and DAGK7rev (5'AGCTAAATCATTGCCAAGGG) that span exon b and EST-S4 was performed. The PCR conditions included an initial hot-start at 94° C. for 5 minutes, followed by 35 cycles at 94° C. for 1 minute, 56° C. for 1 minute and 72° C. for 1 minute and terminated by 5 minutes at 72° C. The resulting PCR amplicon was separated on a 2% agarose gel and shown to be of 246 bp.

The transcript was successfully amplified in both human adult and foetal brain polyA+RNA (Clontech) RT-PCR reactions. As a control the human genomic DNA was also amplified, yielding a fragment of the same length. The results indicate that the EST-S4 might correspond to the 3'-UTR of a new splice variant (FIG. 1, panel A). Thus the shortest form of hDAGKβ protein encoded by the splice variant transcripts is herein designated as SV-hDAGKβ.

In order to further confirm the existence of an alternative splicing event giving rise to a 3' splice variant hDAGKβ isoform a 3' rapid amplification of cDNA ends (RACE) strategy (19) was applied to physically identify and clone the relevant transcript portion in the form of cDNA. Briefly, human foetal brain polyadenylated RNA was reverse transcribed using the anchor oligonucleotide CCAGTGAGCAGAGTGACGAGGACTCGAGCTCAAGC(T)$_1$ as a primer for first strand cDNA synthesis. The resulting cDNA was employed as a template for two nested rounds of PCR employing anchor-specific and gene-specific primers (first round RACE: CCAGTGAGCAGAGTGACG and TCAGAGCCACTACATTTAGGT; second round RACE: GAGGACTCGAGCTCAAGC and AGGTTGTAGACATTATATACC). PCR conditions for both rounds were: 94° C. for 3 minutes (hot start); 25 cycles of (94° C. for 30", 56° C. for 30", 72° C. for 30") followed by a 72° C. for 10' step. Two RACE products, of 200 bp and 750 bp respectively, were obtained and cloned into appropriate E. coli plasmid cloning vectors. Double-pass sequencing confirmed the identity of the two products as two alternatively spliced transcripts bearing the 3' end of the human DAGKβ splice variant coding sequence (with two predicted in-frame translational stop codons at position 2320 and 2365) and ca. 100 bp or ca. 650 bp (owing to two alternatively used polyadenylation signals) of 3' untranslated sequence (UTR). Thus hDAGKβ splice variant transcripts run out of the penultimate coding exon into the last intron of the DAGKβ locus, terminating at two alternatively used polyadenylation signals. The predicted protein encoded by the splice variant transcripts (Seq ID No 4) lacks the last 30 amino acids present in the longest (direct human orthologue of the rat DAGKβ) variant.

Physical Cloning of the Full Length Sequence of Human hDAGKβ and SV-hDAGKβ cDNAs In order to clone the full length cDNA sequence encoding the two DAGKβ variants, the sequence information derived from the in silico and cloning analyses was employed to design PCR primers comprising the initiation codon of the protein (common to both variants) and the sequence immediately 3' of the predicted translational stop codons of each variant. These primers were employed in two successive rounds of nested long-range PCR (LR-PCR) employing a proofreading thermostable polymerase (XL-PCR kit, Perkin Elmer, Calif.) according to manufacturer's instructions. First round PCR conditions were as follows: 94° C. for 3 minutes (hot start); 35 cycles of (94° C. for 30", 55° C. for 30", 72° C. for 5') followed by a 72° C. for 20' step. Second round PCR was carried out on a 1 µl aliquot of a 1:10 dilution of first round PCR using the same conditions as for first round PCR, except that cycling was for 25 cycles. Primers were as detailed in Table 1. The resulting PCR-amplified products (ca. 2.4 kb) were cloned into appropriate plasmid cloning vectors and subjected to double pass sequence analysis. This exercise confirmed the cDNA sequence predicted by the in silico analysis and extended it by revealing the presence of three alternatively spliced exons within hDAGKβ and SV-hDAGKβ transcripts and derived cDNAs (FIG. 5).

Alternative Transcript Splicing Generates Several Isoforms of the hDAGKβ and SV-hDAGKβ

Figure 2A:
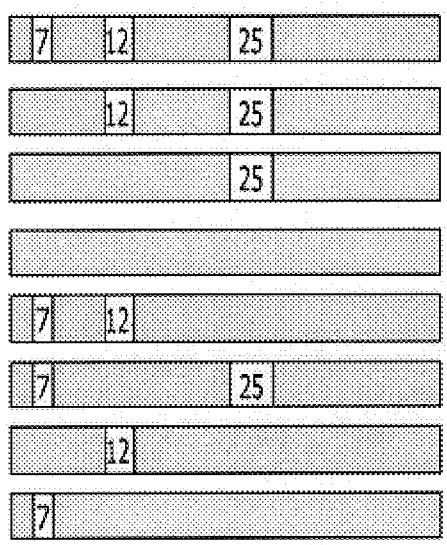
FIGS. 2A and 2B show the position of the alternatively spliced exons that generate a family of hDAGKβ transcripts. The alternatively spliced exons are illustrated as white boxes. The dashed box identifies the SV-DAGKβ transcripts. Panel A: hDAGKβ transcripts generated through alternative splicing. Panel B: SV-hDAGKβ transcripts generated through alternative splicing.
Figure 2B:
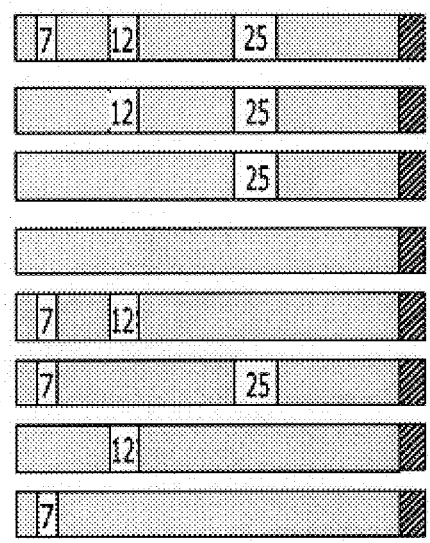

Sequence analysis of the cloned full length cDNAs revealed the presence of three alternatively spliced exons (encoding amino acid sequences of 7, 12 and 25 residues respectively) in addition to the previously characterized alternative splicing event leading to the generation of SV-hDAGKβ transcripts (FIG. 2). Thus at least 8 hDAGKβ isoforms and 8 SV-hDAGKβ isoforms are predicted.

Expression of hDAGKβ and SV-hDAGKβ Transcripts in Adult Human Tissues

Figure 3:
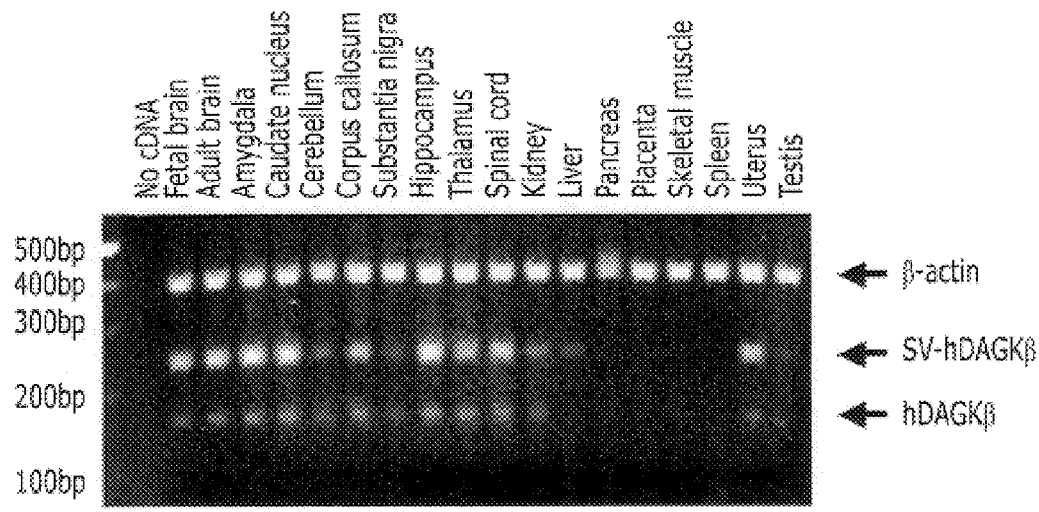
FIG. 3 shows RT-PCR analysis of the expression of hDAGKβ and SV-hDAGKβ in human tissue cDNAs. PCR reactions were carried out separately for each primer pair (hDAGKβ, SV-hDAGKβ and β-actin control) on the indicated tissue cDNAs, and reactions corresponding to the same tissue template were loaded in the same well.

The specificity of hDAGKβ and SV-hDAGKβ expression in adult human tissues was investigated by RT-PCR. Polyadenylated RNA for a variety of human tissues was obtained from a commercial source (Clontech, Calif.). This material was converted to cDNA and a set of PCR primers capable of selectively amplifying either the hDAGKβ or the SV isoform were employed in an RT-PCR study. A set of β-actin specific primers were employed to control the efficacy of the RT-PCR process. Table 1 provides the details of the primers. PCR conditions were: 94° C. for 3 minutes (hot start); 40 cycles of (94° C. for 30", 56° C. for 30", 72° C. for 30") followed by a 72° C. for 10' step. The results (FIG. 3) indicate that both hDAGKβ and SV-hDAGKβ are coordinately expressed in all tissues of neuronal origin (brain regions and spinal cord). Non-neuronal tissues (with the exception of the uterus) do not express significant levels of hDAGKβ transcripts.

TABLE 1

PCR primers used in the present study. A. PCR primers employed for the amplification of full length hDAGKβ cDNAs. The initiation (start) codon is underlined. B. PCR primers for the analysis of expression of h DAGKβ and SV-hDAGKβ isoforms. Sizes of expected products are indicated.

A

| DAGKβ transcript | First round | Second round |
| --- | --- | --- |
| hDAGKβ | CACCACC<u>ATG</u>ACAAACCAGG and TCTAAGAGTGAAACAACACAC | <u>ATG</u>ACAAACCAGGAAAAATGG and AGGATTATTCCTTGCTTCGG |
| SV-hDAGKβ | CACCACC<u>ATG</u>ACAAACCAGG and AGCTAAATCATTGCCAAGG | <u>ATG</u>ACAAACCAGGAAAAATGG and TCTACAACCTAAATGTAGTGG |

B

| DAGKβ transcript | Primers | amplified product (bp) |
| --- | --- | --- |

TABLE 1-continued

PCR primers used in the present study. A. PCR primers employed for the amplification of full length hDAGKβ cDNAs. The initiation (start) codon is underlined. B. PCR primers for the analysis of expression of h DAGKβ and SV-hDAGKβ isoforms. Sizes of expected products are indicated.

| | | |
|---|---|---|
| hDAKGβ | TGCCAATGCAAATTGA and AGGATTATTCCTTGCTTCGG | 153 |
| SV-hDAGKβ | TGCCAATGCAAATTGA and AGCTAAATCATTGCCAAG | 246 |
| β-actin | TGAACCCTAAGGCCAACCGTG and GCTCATAGCTCTTCTCCAGGG | 400 |

Expression of hDAGKβ Transcripts in Normal Vs Neuropathological Conditions

The association between the hDAGKβ and the disorders arising from abnormal expression/activity of hDAGKβ protein and variants thereof can be illustrated by the following experiments.

Figure 4:
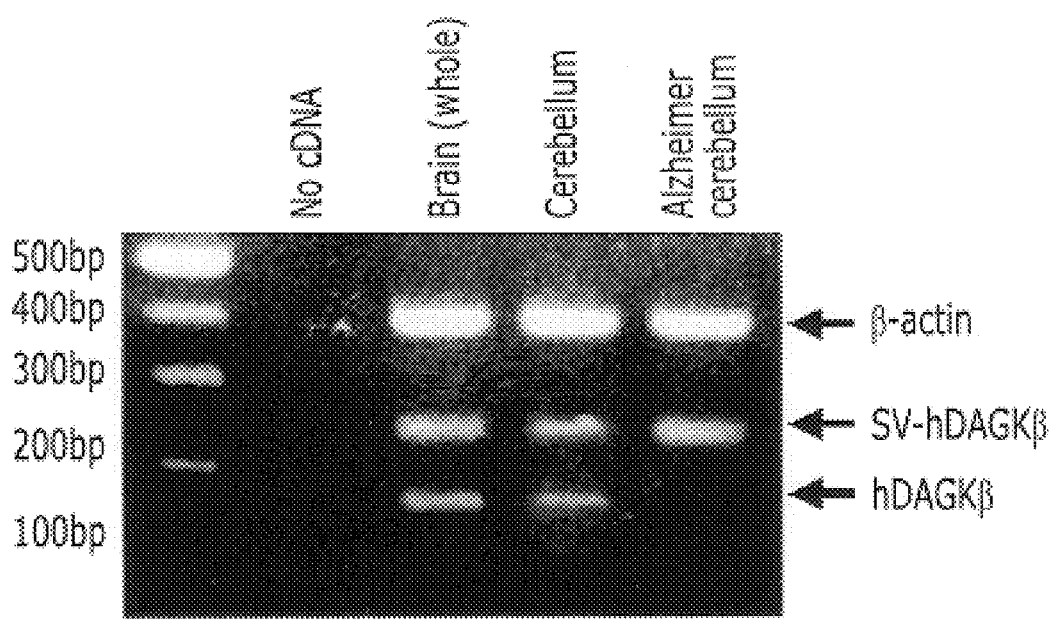
FIG. 4 shows RT-PCR analysis of hDAGKβ and SV-hDAGKβ expression in normal and Alzheimer cerebellum. β-actin was used as a control of RNA levels in the samples.

The expression of hDAGKβ transcripts in normal and pathological conditions of relevance to the present patent was initiated by analyzing hDAGKβ expression by RT-PCR in cDNA from the cerebellum of normal individuals and Alzheimer cerebellum. An initial analysis was carried out using a set of hDAGKβ specific and SV-hDAGKβ specific primers and PCR conditions as detailed in the above section. The results (FIG. 4) indicate that expression of hDAGKβ is lost in Alzheimer cerebellum, while expression of SV-hDAGKβ is unchanged.

Screening for Compounds which Exhibit hDAGKβ Modulating Activity

To identify modulators of hDAGK activity (especially hDAGKβ) activity like inhibitors and activators, respectively, a cellular homogenate containing the hDAGK polypeptide (either from cells transfected with the DAGK cDNA or from overproducing organisms) is incubated with substrates (like DAG and ATP) in the absence or the presence of a chemical entity or crude natural extract that might modulate hDAGK activity (primary screening). The activity of the hDAGK polypeptide or a purified preparation of hDAGK polypeptide in the reaction mixture can be quantified by measuring the ATP-dependent phosphorylation of the DAG substrate employing radio-labelled ATP as substrate (20). The labelled product (phosphatidic acid) is extracted into acidified organic solvents and quantitated by scintillation counting. For more accurate determinations the phosphatidic acid product can also be separated from the mixture by TLC methods and the corresponding radioactive bands can be quantified by using a phosphoimager system. Fluorescence or chemiluminescence-tagged DAG can also be used as the substrate for hDAGK. In this case, the PA product will become labelled with the selected probe and can be separated from the substrate donor molecule by TLC and quantified via densitometric analysis of fluorescent or chemoluminescent spots.

This application also relates to a method of identifying a compound or a composition that can activate or inhibit the activity of the promoter for the DNA of the present invention, which comprises (i) adding a test compound to a cell line whose hDAGK gene has been inactivated by introducing a reporter gene, e.g., the beta-galactosidase from E. coli origin (lacZ); (ii) determining if transcription of the reporter gene occurs by measuring the level of activation of lacZ gene using the chromogenic substrate X-gal using high-throughput calorimetric measurements. The compounds or compositions which are able to inhibit or activate the promoter for the hDAGKβ DNA will alter the expression of the reporter gene. Compounds identified in this way are then tested in vivo to assess their ability to modulate the level of the expression of hDAGK, especially hDAGKβ, in mice CNS.

It is to be understood that modifications and/or alterations to the aspects of the invention specifically disclosed within this application, which based upon the disclosure herein would be readily apparent to a person skilled in the art, are also considered to be included within the scope of the invention as outlined in the appended claims.

REFERENCES

1. Sakane F., Kai, M., Wada, I., Imai, S., Kanoh, H. (1996). The C-terminal part of diacylglycerol kinase α lacking zinc fingers serves as a catalytic domain. Biochem. J. 318, 583–590.
2. Sakane, F. and Kanoh, H. (1997). Molecules in focus: diacylglycerol kinase. Int. J. Biochem. Cell Biol., 19,1139–1143.
3. Goto, K. and Kondo, H. (1993). Molecular cloning and expression of a 90-kDa diacylglycerol kinase that predominantly localizes in neurons. Proc. Natl. Acad. Sci. 90, 7598–7602.
4. Heimer, L., Zahm, D. S., Alheid, G. F. (1995). Basal ganglia. In: G. Paxinos "The rat nervous system" Academic Press, San Diego, pp.579–628
5. Fisher, S. K., Heacock, A. M., Agranoff, B. W. (1992). Inositol lipids and signal transduction in the nervous system: an update. J. Neurochem. 58,18–38.
6. Yuan, PX, Chen, G., Huang, L. D., Manji, H. K. (1998). Lithium stimulates gene expression through the AP-1 transcription factor pathway. Mol. Brain. Res. 58,225–230.
7. Sambrook, J., Fritsch, E. F. and Maniatis, T. Molecular Cloning: a Laboratory Manual. $2^{nd}$ Edition. CSH Laboratory Press. (1989)
8. Boguski, M. S., Lowe, T. M. and Tolstohev, C. M. (1993) dbEST: database for 'Expressed Sequence Tags' Nature Genetics, 4, 332–333.
9. Altschul, S. F., Warren, G., Webb, M., Myers, E. W., and Lipman, D. J., (1990). Basic local alignment search tool. J. Mol. Biol., 215, 403–410.
10. Wootton, J. C. and Federhen S.,(1993). Statistics of local complexity in amino acid sequences and sequence databases. Comput. Chem. 17,149–163
11. Wootton, J. C. (1994). Non-globular domains in protein sequences: aoutomated segmentation using complexity measures. Comput. Chem. 18, 269.
12. Kamb, A., Wang, C., Thomas, A., DeHoff, B. S., Norris, F. H., Richardson, K., Rine, J., Skolnick, M. H. and Rosteck Jr., P. R. (1995). Software trapping: a strategy for 13. Borodovsky, M. and Mc Ininch J. D., (1993). Parallel gene recognition for both DNA strands. *Computers and Chemistry* 17, 123–133
14. Uberbacher, E. C., and Mural, R. J., (1991). Locating protein-coding regions in Human DNA sequences by a multiple sensors-neural network approach. *Proc. Natl. Accad. Sci. USA*, 88, 11261–11265
15. Schuler, G. D. (1998). Electronic PCR: bridging the gap between genome mapping and genome sequencing. *Trends in Biotech.* 16, 456–459.
16 Kawasaki E S. (1990). Amplification of RNA. In: PCR protocols, a guide to methods and applications. Eds Innis, Gelfand, Sninsky and White. Acad. Press.
17. Trower M K., Burt D., Purvis I J., Dykes C W. & Christodoulou C. (1995). Fluorescent dye-primer cycle sequencing using non-purified PCR products as templates; development of a protocol amenable to high-throughput DNA sequencing. *Nucleic Acids Research*, 23, 2348–2349
18. Higgins, D. G. and Sharp, P. M. (1988). CLUSTAL: a package for performing multiple sequence alignments on a microcomputer. *Gene* 73, 237–244.
19 Frohman, M A (1993). Rapid amplification of complementary DNA ends for generation of full-length complementary DNAs: thermal RACE. Methods Enzymol, 218, 340–56
20. Kanoh, H., Sakane, F., Yamada, K. (1992). Diacylglycerol kinase isozymes from brain and lymphoid tissues. *Methods Enzymol.* 209, 162–172.

What is claimed is:

1. An isolated human diacylglcerol kinase β (hDAGKβ) protein comprising the amino acid sequence encoded by SEQ ID NO:4.

2. A method for identifying a compound with DAGK modulating activity, comprising contacting a DAGK protein encoded by SEQ ID NO:4 with a test compound and detecting modulation of enzyme activity or detecting enzyme inactivity.

3. A method of producing an hDAGKβ protein comprising introducing a vector comprising a nucleotide sequence encoding a hDAGKβ protein of claim 1 into a cell, and culturing said cell under conditions suitable for expression of said hDAGKβ protein.

* * * * *

SEQUENCE LISTING

```
<160> NUMBER OF SEQ ID NOS: 7

<210> SEQ ID NO 1
<211> LENGTH: 3926
<212> TYPE: DNA
<213> ORGANISM: Homo sapiens
<220> FEATURE:
<221> NAME/KEY: CDS
<222> LOCATION: (1)..(2415)

<400> SEQUENCE: 1 atg aca aac cag gaa aaa tgg gcc cac ctc agc cct tcg gaa ttt tcc      48
Met Thr Asn Gln Glu Lys Trp Ala His Leu Ser Pro Ser Glu Phe Ser
  1               5                  10                  15 caa ctt cag aaa tat gct gag tat tct aca aag aaa tta aag gat gtt      96
Gln Leu Gln Lys Tyr Ala Glu Tyr Ser Thr Lys Lys Leu Lys Asp Val
             20                  25                  30 ctt gaa gaa ttc cat ggt aat ggt gtg ctt gca aag tat aat cct gaa     144
Leu Glu Glu Phe His Gly Asn Gly Val Leu Ala Lys Tyr Asn Pro Glu
         35                  40                  45 ggg aaa caa gac att ctt aac caa aca ata gat ttt gaa ggt ttc aaa     192
Gly Lys Gln Asp Ile Leu Asn Gln Thr Ile Asp Phe Glu Gly Phe Lys
     50                  55                  60 cta ttc atg aag aca ttc ctg gaa gcc gag ctt cct gat gat ttc act     240
Leu Phe Met Lys Thr Phe Leu Glu Ala Glu Leu Pro Asp Asp Phe Thr
 65                  70                  75                  80 gca cac ctt ttc atg tca ttt agc aac aag ttt cct cat tct agt cca     288
Ala His Leu Phe Met Ser Phe Ser Asn Lys Phe Pro His Ser Ser Pro
                 85                  90                  95 atg gta aaa agt aag cct gct ctc cta tca ggc ggt ctg aga atg aat     336
Met Val Lys Ser Lys Pro Ala Leu Leu Ser Gly Gly Leu Arg Met Asn
            100                 105                 110 aaa ggt gcc atc acc cct ccc cga act act tct cct gca aat acg tgt     384
Lys Gly Ala Ile Thr Pro Pro Arg Thr Thr Ser Pro Ala Asn Thr Cys
        115                 120                 125 tcc cca gaa gta atc cat ctg aag gac att gtc tgt tac ctg tct ctg     432
Ser Pro Glu Val Ile His Leu Lys Asp Ile Val Cys Tyr Leu Ser Leu
    130                 135                 140 ctt gaa aga gga aga cct gag gat aag ctt gag ttt atg ttt cgc ctt     480
Leu Glu Arg Gly Arg Pro Glu Asp Lys Leu Glu Phe Met Phe Arg Leu
145                 150                 155                 160 tat gac acg gat ggg aat ggc ttc ctg gac agc tcg gag cta gaa aat     528
Tyr Asp Thr Asp Gly Asn Gly Phe Leu Asp Ser Ser Glu Leu Glu Asn
                165                 170                 175
```

```
atc atc agt cag atg atg cat gtt gca gaa tac ctt gag tgg gat gtc    576
Ile Ile Ser Gln Met Met His Val Ala Glu Tyr Leu Glu Trp Asp Val
            180                 185                 190 act gaa ctt aat cca atc ctc cat gaa atg atg gaa gaa att gac tat    624
Thr Glu Leu Asn Pro Ile Leu His Glu Met Met Glu Glu Ile Asp Tyr
        195                 200                 205 gat cat gat gga acc gtg tct ctg gag gaa tgg att caa gga gga atg    672
Asp His Asp Gly Thr Val Ser Leu Glu Glu Trp Ile Gln Gly Gly Met
210                 215                 220 aca acg att cca ctt ctt gtg ctc ctg ggc tta gaa aat aac gtg aag    720
Thr Thr Ile Pro Leu Leu Val Leu Leu Gly Leu Glu Asn Asn Val Lys
225                 230                 235                 240 gat gat gga cag cac gtg tgg cga ctg aag cac ttt aac aaa cct gcc    768
Asp Asp Gly Gln His Val Trp Arg Leu Lys His Phe Asn Lys Pro Ala
                245                 250                 255 tat tgc aac ctt tgc ctg aac atg ctg att ggc gtg ggg aag cag ggc    816
Tyr Cys Asn Leu Cys Leu Asn Met Leu Ile Gly Val Gly Lys Gln Gly
            260                 265                 270 ctc tgc tgt tcc ttc tgc aag tac aca gtc cat gag cgc tgt gtg gct    864
Leu Cys Cys Ser Phe Cys Lys Tyr Thr Val His Glu Arg Cys Val Ala
        275                 280                 285 cga gca cct ccc tct tgc atc aag acc tat gtg aag tcc aaa agg aac    912
Arg Ala Pro Pro Ser Cys Ile Lys Thr Tyr Val Lys Ser Lys Arg Asn
290                 295                 300 act gat gtc atg cac cat tac tgg gtt gaa ggt aac tgc cca acc aag    960
Thr Asp Val Met His His Tyr Trp Val Glu Gly Asn Cys Pro Thr Lys
305                 310                 315                 320 tgt gat aag tgc cac aaa act gtt aaa tgt tac cag ggc ctg aca gga   1008
Cys Asp Lys Cys His Lys Thr Val Lys Cys Tyr Gln Gly Leu Thr Gly
                325                 330                 335 ctg cat tgt gtt tgg tgt cag atc aca ctg cat aat aaa tgt gct tct   1056
Leu His Cys Val Trp Cys Gln Ile Thr Leu His Asn Lys Cys Ala Ser
            340                 345                 350 cat cta aaa cct gaa tgt gac tgt gga cct ttg aag gac cat att tta   1104
His Leu Lys Pro Glu Cys Asp Cys Gly Pro Leu Lys Asp His Ile Leu
        355                 360                 365 cca ccc aca aca atc tgt cca gtg gta ctg cag act ctg ccc act tca   1152
Pro Pro Thr Thr Ile Cys Pro Val Val Leu Gln Thr Leu Pro Thr Ser
370                 375                 380 gga gtt tca gtt cct gag gaa aga caa tca aca gtg aaa aag gaa aag   1200
Gly Val Ser Val Pro Glu Glu Arg Gln Ser Thr Val Lys Lys Glu Lys
385                 390                 395                 400 agt ggt tcc cag cag cca aac aaa gtg att gac aag aat aaa atg caa   1248
Ser Gly Ser Gln Gln Pro Asn Lys Val Ile Asp Lys Asn Lys Met Gln
                405                 410                 415 aga gcc aac tct gtt act gta gat gga caa ggc ctg cag gtc act cct   1296
Arg Ala Asn Ser Val Thr Val Asp Gly Gln Gly Leu Gln Val Thr Pro
            420                 425                 430 gtg cct ggt act cac cca ctt tta gtt ttt gtg aac ccc aaa agt ggt   1344
Val Pro Gly Thr His Pro Leu Leu Val Phe Val Asn Pro Lys Ser Gly
        435                 440                 445 gga aaa caa gga gaa cga att tac aga aaa ttc cag tat cta tta aat   1392
Gly Lys Gln Gly Glu Arg Ile Tyr Arg Lys Phe Gln Tyr Leu Leu Asn
450                 455                 460 cct cgt cag gtt tac agt ctt tct gga aat gga cca atg cca ggg tta   1440
Pro Arg Gln Val Tyr Ser Leu Ser Gly Asn Gly Pro Met Pro Gly Leu
465                 470                 475                 480 aac ttt ttc cgt gat gtt cct gac ttc aga gtt tta gcc tgt ggt gga   1488
Asn Phe Phe Arg Asp Val Pro Asp Phe Arg Val Leu Ala Cys Gly Gly
                485                 490                 495
```

```
gat gga acc gtg ggc tgg gtt ttg gat tgc ata gaa aag gcc aat gta      1536
Asp Gly Thr Val Gly Trp Val Leu Asp Cys Ile Glu Lys Ala Asn Val
            500                 505                 510 ggc aag cat cct cca gtt gcg att ctg cct ctt ggg act ggc aat gat      1584
Gly Lys His Pro Pro Val Ala Ile Leu Pro Leu Gly Thr Gly Asn Asp
        515                 520                 525 cta gca aga tgc ctg cga tgg gga gga ggt tac gaa ggt gag aat ctg      1632
Leu Ala Arg Cys Leu Arg Trp Gly Gly Gly Tyr Glu Gly Glu Asn Leu
    530                 535                 540 atg aaa att cta aaa gac att gaa aac agc aca gaa atc atg ttg gac      1680
Met Lys Ile Leu Lys Asp Ile Glu Asn Ser Thr Glu Ile Met Leu Asp
545                 550                 555                 560 agg tgg aag ttt gaa gtc ata cct aat gac aaa gat gag aaa gga gac      1728
Arg Trp Lys Phe Glu Val Ile Pro Asn Asp Lys Asp Glu Lys Gly Asp
            565                 570                 575 cca gtg cct tac agt atc atc aat aat tac ttt tcc att ggc gtg gat      1776
Pro Val Pro Tyr Ser Ile Ile Asn Asn Tyr Phe Ser Ile Gly Val Asp
        580                 585                 590 gcc tcc att gca cac aga ttc cac atc atg aga gaa aaa cac cca gag      1824
Ala Ser Ile Ala His Arg Phe His Ile Met Arg Glu Lys His Pro Glu
    595                 600                 605 aaa ttc aac agt aga atg aag aac aaa ttt tgg tat ttt gag ttt ggc      1872
Lys Phe Asn Ser Arg Met Lys Asn Lys Phe Trp Tyr Phe Glu Phe Gly
610                 615                 620 aca tct gaa act ttc tca gcc acc tgc aag aag cta cat gaa tct gta      1920
Thr Ser Glu Thr Phe Ser Ala Thr Cys Lys Lys Leu His Glu Ser Val
            625                 630                 635                 640 gaa ata gaa tgt gat gga gta cag ata gat tta ata aac atc tct ctg      1968
Glu Ile Glu Cys Asp Gly Val Gln Ile Asp Leu Ile Asn Ile Ser Leu
        645                 650                 655 gaa gga att gct att ttg aat ata cca agc atg cat gga gga tcc aat      2016
Glu Gly Ile Ala Ile Leu Asn Ile Pro Ser Met His Gly Gly Ser Asn
    660                 665                 670 ctt tgg gga gag tct aag aaa aga cga agc cat cga cga ata gag aaa      2064
Leu Trp Gly Glu Ser Lys Lys Arg Arg Ser His Arg Arg Ile Glu Lys
675                 680                 685 aaa ggg tct gac aaa agg acc acc gtc aca gat gcc aaa gag ttg aag      2112
Lys Gly Ser Asp Lys Arg Thr Thr Val Thr Asp Ala Lys Glu Leu Lys
            690                 695                 700 ttt gca agt caa gat ctc agt gac cag ctg ctg gag gtg gtc ggc ttg      2160
Phe Ala Ser Gln Asp Leu Ser Asp Gln Leu Leu Glu Val Val Gly Leu
705                 710                 715                 720 gaa gga gcc atg gag atg ggg caa ata tac aca ggc ctg aaa agt gct      2208
Glu Gly Ala Met Glu Met Gly Gln Ile Tyr Thr Gly Leu Lys Ser Ala
            725                 730                 735 ggc cgg cgg ctg gct cag tgc tcc tgc gtg gtc atc agg acg agc aag      2256
Gly Arg Arg Leu Ala Gln Cys Ser Cys Val Val Ile Arg Thr Ser Lys
        740                 745                 750 tct ctg cca atg caa att gat ggg gag cca tgg atg cag acc cca tgc      2304
Ser Leu Pro Met Gln Ile Asp Gly Glu Pro Trp Met Gln Thr Pro Cys
    755                 760                 765 aca ata aaa att aca cac aag aac caa gcc cca atg ctg atg ggc ccg      2352
Thr Ile Lys Ile Thr His Lys Asn Gln Ala Pro Met Leu Met Gly Pro
770                 775                 780 cct cca aaa acc ggt tta ttc tgc tcc ctc gtc aaa agg aca aga aac      2400
Pro Pro Lys Thr Gly Leu Phe Cys Ser Leu Val Lys Arg Thr Arg Asn
785                 790                 795                 800 cga agc aag gaa taa tcctgtgttg tttcactctt agaaattgaa ttagcataat      2455
Arg Ser Lys Glu
```

-continued

```
tgggccatgg aacacatatg ctggaaatct ttgaaccatt tcaagtctcc tgctcatgca    2515
aaatcatgga agtggtttaa cagttttttgt tactaagcta atgtaaaatt cagctattag    2575
aaaatttatt gtctcagttt ttataggcat ctttgcatga agaaagcaga agtttacctg    2635
aagtgatact gcatattttt ggtgcatgca ttcccataga ttttacatc tcccacccaa    2695 ctcttcccca atttccttttt actaacctgt gagaaaaacc cgtgaaacat gaaaaggaa    2755 ataccatggg aaacgtgatt ctcagtgtga ttccaattat tacgaagcac taatcagtaa    2815
cgctacaatg atcataattg cagattgcta tacgtttccc ttttagaatc agtgtatcag    2875
tgacctatga cttgaggaga aactttttaat tcgaagattt tattaaatag ttgactacaa    2935
taccttgcta tatatacata gttttttcttc aacatcttaa ctcttctgag tggaaataaa    2995
aatatcaggc ataaggtttt ctcatgctga aaaatagaac gcggttttta ttttgcttag    3055 ttttctttttt aattccagaa ataagtgaaa acatgttact tgacagtcaa gtgtggtaat    3115
atggcaagcc ttgttccttt ctgcatgaga atctaggaga gaattcataa ccacaccaat    3175
aacgaaatag aagttttaaa ctatgtgcct aatcaatgtg tttcccacca aagattcaga    3235
aaacaatgct tgagagaaat gggttaatgc ataattaatt aagcattgtg gagcaaattt    3295
agggttcctg tgattaattt tgtgatgact aaaatgctgg aaagcaagtg agttgcccat    3355
taattatgat taaaattctc acctttcaca gacagacaat aagccagaca acacaatcaa    3415
agctcaatag atgatttctt gcttttttca gtcatttata aatataggtg taattttttca    3475 tggatcagtt aagtacactt gaaggaagta aatgattgta tcagtttatt tctagtataa    3535
atgggtacct gtaataatac tgagctcttg gaagcgaatc atgcatgcaa ttagctccct    3595
cctcctcacc tactccactc ccatctttat gacatttcaa atgtttattt ggaaacaaca    3655
gcctagatca ctgttgaagg tgttcatggc atagttggag tctctgactg tttaaagaaa    3715
tcacagaaca gtacttttct tttagtgttt cattaagcct atgatgtaaa atgaaatgct    3775
tctgagcagt cttgtaatat tgttcattca tattgacctg catctcatca ttgcatgttt    3835
tatgttttca aacatgccat aaggaaaacg agtgcctgaa ctgcatgatt tattagtttc    3895
tctccactct gcattaaagt gctaatgatt t                                    3926
```

<210> SEQ ID NO 2
<211> LENGTH: 804
<212> TYPE: PRT
<213> ORGANISM: Homo sapiens

<400> SEQUENCE: 2

Met Thr Asn Gln Glu Lys Trp Ala His Leu Ser Pro Ser Glu Phe Ser
 1               5                  10                  15

Gln Leu Gln Lys Tyr Ala Glu Tyr Ser Thr Lys Lys Leu Lys Asp Val
             20                  25                  30

Leu Glu Glu Phe His Gly Asn Gly Val Leu Ala Lys Tyr Asn Pro Glu
         35                  40                  45

Gly Lys Gln Asp Ile Leu Asn Gln Thr Ile Asp Phe Glu Gly Phe Lys
     50                  55                  60

Leu Phe Met Lys Thr Phe Leu Glu Ala Glu Leu Pro Asp Asp Phe Thr
 65                  70                  75                  80

Ala His Leu Phe Met Ser Phe Ser Asn Lys Phe Pro His Ser Ser Pro
                 85                  90                  95

Met Val Lys Ser Lys Pro Ala Leu Leu Ser Gly Gly Leu Arg Met Asn
            100                 105                 110

-continued

```
Lys Gly Ala Ile Thr Pro Pro Arg Thr Thr Ser Pro Ala Asn Thr Cys
        115                 120                 125

Ser Pro Glu Val Ile His Leu Lys Asp Ile Val Cys Tyr Leu Ser Leu
    130                 135                 140

Leu Glu Arg Gly Arg Pro Glu Asp Lys Leu Glu Phe Met Phe Arg Leu
145                 150                 155                 160

Tyr Asp Thr Asp Gly Asn Gly Phe Leu Asp Ser Ser Glu Leu Glu Asn
                165                 170                 175

Ile Ile Ser Gln Met Met His Val Ala Glu Tyr Leu Glu Trp Asp Val
            180                 185                 190

Thr Glu Leu Asn Pro Ile Leu His Glu Met Met Glu Glu Ile Asp Tyr
        195                 200                 205

Asp His Asp Gly Thr Val Ser Leu Glu Glu Trp Ile Gln Gly Gly Met
    210                 215                 220

Thr Thr Ile Pro Leu Leu Val Leu Leu Gly Leu Glu Asn Asn Val Lys
225                 230                 235                 240

Asp Asp Gly Gln His Val Trp Arg Leu Lys His Phe Asn Lys Pro Ala
                245                 250                 255

Tyr Cys Asn Leu Cys Leu Asn Met Leu Ile Gly Val Gly Lys Gln Gly
            260                 265                 270

Leu Cys Cys Ser Phe Cys Lys Tyr Thr Val His Glu Arg Cys Val Ala
        275                 280                 285

Arg Ala Pro Pro Ser Cys Ile Lys Thr Tyr Val Lys Ser Lys Arg Asn
    290                 295                 300

Thr Asp Val Met His His Tyr Trp Val Glu Gly Asn Cys Pro Thr Lys
305                 310                 315                 320

Cys Asp Lys Cys His Lys Thr Val Lys Cys Tyr Gln Gly Leu Thr Gly
                325                 330                 335

Leu His Cys Val Trp Cys Gln Ile Thr Leu His Asn Lys Cys Ala Ser
            340                 345                 350

His Leu Lys Pro Glu Cys Asp Cys Gly Pro Leu Lys Asp His Ile Leu
        355                 360                 365

Pro Pro Thr Thr Ile Cys Pro Val Val Leu Gln Thr Leu Pro Thr Ser
    370                 375                 380

Gly Val Ser Val Pro Glu Glu Arg Gln Ser Thr Val Lys Lys Glu Lys
385                 390                 395                 400

Ser Gly Ser Gln Gln Pro Asn Lys Val Ile Asp Lys Asn Lys Met Gln
                405                 410                 415

Arg Ala Asn Ser Val Thr Val Asp Gly Gln Gly Leu Gln Val Thr Pro
            420                 425                 430

Val Pro Gly Thr His Pro Leu Leu Val Phe Val Asn Pro Lys Ser Gly
        435                 440                 445

Gly Lys Gln Gly Glu Arg Ile Tyr Arg Lys Phe Gln Tyr Leu Leu Asn
    450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
            500                 505                 510

Gly Lys His Pro Pro Val Ala Ile Leu Pro Leu Gly Thr Gly Asn Asp
        515                 520                 525
```

-continued

Leu Ala Arg Cys Leu Arg Trp Gly Gly Tyr Glu Gly Glu Asn Leu
    530                 535                 540

Met Lys Ile Leu Lys Asp Ile Glu Asn Ser Thr Glu Ile Met Leu Asp
545                 550                 555                 560

Arg Trp Lys Phe Glu Val Ile Pro Asn Asp Lys Asp Glu Lys Gly Asp
                565                 570                 575

Pro Val Pro Tyr Ser Ile Ile Asn Asn Tyr Phe Ser Ile Gly Val Asp
            580                 585                 590

Ala Ser Ile Ala His Arg Phe His Ile Met Arg Glu Lys His Pro Glu
        595                 600                 605

Lys Phe Asn Ser Arg Met Lys Asn Lys Phe Trp Tyr Phe Glu Phe Gly
    610                 615                 620

Thr Ser Glu Thr Phe Ser Ala Thr Cys Lys Lys Leu His Glu Ser Val
625                 630                 635                 640

Glu Ile Glu Cys Asp Gly Val Gln Ile Asp Leu Ile Asn Ile Ser Leu
                645                 650                 655

Glu Gly Ile Ala Ile Leu Asn Ile Pro Ser Met His Gly Gly Ser Asn
            660                 665                 670

Leu Trp Gly Glu Ser Lys Lys Arg Arg Ser His Arg Arg Ile Glu Lys
        675                 680                 685

Lys Gly Ser Asp Lys Arg Thr Thr Val Thr Asp Ala Lys Glu Leu Lys
    690                 695                 700

Phe Ala Ser Gln Asp Leu Ser Asp Gln Leu Leu Glu Val Val Gly Leu
705                 710                 715                 720

Glu Gly Ala Met Glu Met Gly Gln Ile Tyr Thr Gly Leu Lys Ser Ala
                725                 730                 735

Gly Arg Arg Leu Ala Gln Cys Ser Cys Val Val Ile Arg Thr Ser Lys
            740                 745                 750

Ser Leu Pro Met Gln Ile Asp Gly Glu Pro Trp Met Gln Thr Pro Cys
        755                 760                 765

Thr Ile Lys Ile Thr His Lys Asn Gln Ala Pro Met Leu Met Gly Pro
    770                 775                 780

Pro Pro Lys Thr Gly Leu Phe Cys Ser Leu Val Lys Arg Thr Arg Asn
785                 790                 795                 800

Arg Ser Lys Glu

<210> SEQ ID NO 3
<211> LENGTH: 3926
<212> TYPE: DNA
<213> ORGANISM: Homo sapiens

<400> SEQUENCE: 3
aaatcattag cactttaatg cagagtggag agaaactaat aaatcatgca gttcaggcac    60
tcgtttttcct tatggcatgt ttgaaaacat aaaacatgca atgatgagat gcaggtcaat   120
atgaatgaac aatattacaa gactgctcag aagcatttca ttttacatca taggcttaat   180
gaaacactaa agaaaagta ctgttctgtg atttctttaa acagtcagag actccaacta    240
tgccatgaac accttcaaca gtgatctagg ctgttgtttc caaataaaca tttgaaatgt   300
cataaagatg ggagtggagt aggtgaggag gagggagcta attgcatgca tgattcgctt   360
ccaagagctc agtattatta caggtaccca tttatactag aaataaactg atacaatcat   420
ttacttcctt caagtgtact taactgatcc atgaaaaatt acacctatat ttataaatga   480
ctgaaaaaag caagaaatca tctattgagc tttgattgtg ttgtctggct tattgtctgt   540

-continued

```
ctgtgaaagg tgagaatttt aatcataatt aatgggcaac tcacttgctt tccagcattt      600
tagtcatcac aaaattaatc acaggaaccc taaatttgct ccacaatgct taattaatta      660
tgcattaacc catttctctc aagcattgtt ttctgaatct ttggtgggaa acacattgat      720
taggcacata gtttaaaact tctatttcgt tattggtgtg gttatgaatt ctctcctaga      780
ttctcatgca gaaaggaaca aggcttgcca tattaccaca cttgactgtc aagtaacatg      840
ttttcactta tttctggaat taaaagaaa actaagcaaa ataaaaaccg cgttctattt      900
ttcagcatga gaaaacctta tgcctgatat ttttatttcc actcagaaga gttaagatgt      960
tgaagaaaaa ctatgtatat atagcaaggt attgtagtca actatttaat aaaatcttcg     1020
aattaaaagt ttctcctcaa gtcataggtc actgatacac tgattctaaa agggaaacgt     1080
atagcaatct gcaattatga tcattgtagc gttactgatt agtgcttcgt aataattgga     1140
atcacactga gaatcacgtt tcccatggta ttttccttttt catgtttcac gggttttttct    1200 cacaggttag taaaggaaa ttggggaaga gttgggtggg agatgtaaaa atctatggga     1260
atgcatgcac caaaaatatg cagtatcact tcaggtaaac ttctgctttc ttcatgcaaa     1320
gatgcctata aaaactgaga caataaattt tctaatagct gaatttttaca ttagcttagt    1380 aacaaaaact gttaaaccac ttccatgatt ttgcatgagc aggagacttg aaatggttca     1440
aagatttcca gcatatgtgt tccatggccc aattatgcta attcaattc taagagtgaa      1500 acaacacagg attattcctt gcttcggttt cttgtccttt tgacgaggga gcagaataaa     1560 ccggttttg gaggcgggcc catcagcatt ggggcttggt tcttgtgtgt aattttttatt    1620 gtgcatgggg tctgcatcca tggctcccca tcaatttgca ttggcagaga cttgctcgtc     1680
ctgatgacca cgcaggagca ctgagccagc cgccggccag cacttttcag gcctgtgtat     1740
atttgcccca tctccatggc tccttccaag ccgaccacct ccagcagctg gtcactgaga     1800
tcttgacttg caaacttcaa ctctttggca tctgtgacgg tggtccttt gtcagaccct     1860 tttttctcta ttcgtcgatg gcttcgtctt ttcttagact ctccccaaag attggatcct    1920
ccatgcatgc ttggtatatt caaaatagca attccttcca gagagatgtt tattaaatct   1980
atctgtactc catcacattc tatttctaca gattcatgta gcttcttgca ggtggctgag   2040
aaagtttcag atgtgccaaa ctcaaaatac caaaatttgt tcttcattct actgttgaat   2100
ttctctgggt gttttttctct catgatgtgg aatctgtgtg caatggaggc atccacgcca   2160
atggaaaagt aattattgat gatactgtaa ggcactggg ctccttttctc atctttgtca   2220 ttaggtatga cttcaaactt ccacctgtcc aacatgattt ctgtgctgtt ttcaatgtct    2280
tttagaattt tcatcagatt ctcaccttcg taacctcctc cccatcgcag gcatcttgct    2340
agatcattgc cagtcccaag aggcagaatc gcaactggag gatgcttgcc tacattggcc    2400
ttttctatgc aatccaaaac ccagcccacg gttccatctc caccacaggc taacactctg    2460
aagtcaggaa catcacggaa aaagtttaac cctggcattg gtccatttcc agaaagactg    2520
taaacctgac gaggatttaa tagatactgg aattttctgt aaattcgttc tccttgtttt    2580
ccaccacttt tggggttcac aaaaactaaa agtgggtgag taccaggcac aggagtgacc    2640
tgcaggcctt gtccatctac agtaacagag ttggctcttt gcattttatt cttgtcaatc   2700
actttgtttg gctgctggga accactcttt tccttttca ctgttgattg tctttcctca     2760
ggaactgaaa ctcctgaagt gggcagagtc tgcagtacca ctggacagat tgttgtgggt    2820
ggtaaaatat ggtccttcaa aggtccacag tcacattcag gttttagatg agaagcacat   2880
ttattatgca gtgtgatctg acaccaaaca caatgcagtc ctgtcaggcc ctggtaacat   2940
```

-continued

```
ttaacagttt tgtggcactt atcacacttg gttgggcagt taccttcaac ccagtaatgg    3000
tgcatgacat cagtgttcct tttggacttc ataggtct tgatgcaaga gggaggtgct    3060
cgagccacac agcgctcatg gactgtgtac ttgcagaagg aacagcagag gccctgcttc    3120
cccacgccaa tcagcatgtt caggcaaagg ttgcaatagg caggtttgtt aaagtgcttc    3180
agtcgccaca cgtgctgtcc atcatccttc acgttatttt ctaagcccag gagcacaaga    3240
agtggaatcg ttgtcattcc tccttgaatc cattcctcca gagacacggt tccatcatga    3300
tcatagtcaa tttcttccat catttcatgg aggattggat taagttcagt gacatcccac    3360
tcaaggtatt ctgcaacatg catcatctga ctgatgatat tttctagctc cgagctgtcc    3420
aggaagccat tcccatccgt gtcataaagg cgaaacataa actcaagctt atcctcaggt    3480
cttcctcttt caagcagaga caggtaacag acaatgtcct tcagatggat tacttctggg    3540
gaacacgtat ttgcaggaga agtagttcgg ggagggtga tggcaccttt attcattctc    3600
agaccgcctg ataggagagc aggcttactt tttaccattg gactagaatg aggaaacttg    3660
ttgctaaatg acatgaaaag gtgtgcagtg aaatcatcag gaagctcggc ttccaggaat    3720
gtcttcatga atagtttgaa accttcaaaa tctattgttt ggttaagaat gtcttgtttc    3780
ccttcaggat tatactttgc aagcacacca ttaccatgga attcttcaag aacatccttt    3840
aatttctttg tagaatactc agcatatttc tgaagttggg aaaattccga agggctgagg    3900
tgggcccatt tttcctggtt tgtcat                                          3926
```

<210> SEQ ID NO 4
<211> LENGTH: 3172
<212> TYPE: DNA
<213> ORGANISM: Homo sapiens
<220> FEATURE:
<221> NAME/KEY: CDS
<222> LOCATION: (1)..(2322)

<400> SEQUENCE: 4

```
atg aca aac cag gaa aaa tgg gcc cac ctc agc cct tcg gaa ttt tcc      48
Met Thr Asn Gln Glu Lys Trp Ala His Leu Ser Pro Ser Glu Phe Ser
  1               5                  10                  15 caa ctt cag aaa tat gct gag tat tct aca aag aaa tta aag gat gtt      96
Gln Leu Gln Lys Tyr Ala Glu Tyr Ser Thr Lys Lys Leu Lys Asp Val
             20                  25                  30 ctt gaa gaa ttc cat ggt aat ggt gtg ctt gca aag tat aat cct gaa     144
Leu Glu Glu Phe His Gly Asn Gly Val Leu Ala Lys Tyr Asn Pro Glu
         35                  40                  45 ggg aaa caa gac att ctt aac caa aca ata gat ttt gaa ggt ttc aaa     192
Gly Lys Gln Asp Ile Leu Asn Gln Thr Ile Asp Phe Glu Gly Phe Lys
     50                  55                  60 cta ttc atg aag aca ttc ctg gaa gcc gag ctt cct gat gat ttc act     240
Leu Phe Met Lys Thr Phe Leu Glu Ala Glu Leu Pro Asp Asp Phe Thr
 65                  70                  75                  80 gca cac ctt ttc atg tca ttt agc aac aag ttt cct cat tct agt cca     288
Ala His Leu Phe Met Ser Phe Ser Asn Lys Phe Pro His Ser Ser Pro
                 85                  90                  95 atg gta aaa agt aag cct gct ctc cta tca ggc ggt ctg aga atg aat     336
Met Val Lys Ser Lys Pro Ala Leu Leu Ser Gly Gly Leu Arg Met Asn
            100                 105                 110 aaa ggt gcc atc acc cct ccc cga act act tct cct gca aat acg tgt     384
Lys Gly Ala Ile Thr Pro Pro Arg Thr Thr Ser Pro Ala Asn Thr Cys
        115                 120                 125 tcc cca gaa gta atc cat ctg aag gac att gtc tgt tac ctg tct ctg     432
```

```
Ser Pro Glu Val Ile His Leu Lys Asp Ile Val Cys Tyr Leu Ser Leu
    130                 135                 140 ctt gaa aga gga aga cct gag gat aag ctt gag ttt atg ttt cgc ctt        480
Leu Glu Arg Gly Arg Pro Glu Asp Lys Leu Glu Phe Met Phe Arg Leu
145                 150                 155                 160 tat gac acg gat ggg aat ggc ttc ctg gac agc tcg gag cta gaa aat        528
Tyr Asp Thr Asp Gly Asn Gly Phe Leu Asp Ser Ser Glu Leu Glu Asn
                165                 170                 175 atc atc agt cag atg atg cat gtt gca gaa tac ctt gag tgg gat gtc        576
Ile Ile Ser Gln Met Met His Val Ala Glu Tyr Leu Glu Trp Asp Val
            180                 185                 190 act gaa ctt aat cca atc ctc cat gaa atg atg gaa gaa att gac tat        624
Thr Glu Leu Asn Pro Ile Leu His Glu Met Met Glu Glu Ile Asp Tyr
        195                 200                 205 gat cat gat gga acc gtg tct ctg gag gaa tgg att caa gga gga atg        672
Asp His Asp Gly Thr Val Ser Leu Glu Glu Trp Ile Gln Gly Gly Met
    210                 215                 220 aca acg att cca ctt ctt gtg ctc ctg ggc tta gaa aat aac gtg aag        720
Thr Thr Ile Pro Leu Leu Val Leu Leu Gly Leu Glu Asn Asn Val Lys
225                 230                 235                 240 gat gat gga cag cac gtg tgg cga ctg aag cac ttt aac aaa cct gcc        768
Asp Asp Gly Gln His Val Trp Arg Leu Lys His Phe Asn Lys Pro Ala
                245                 250                 255 tat tgc aac ctt tgc ctg aac atg ctg att ggc gtg ggg aag cag ggc        816
Tyr Cys Asn Leu Cys Leu Asn Met Leu Ile Gly Val Gly Lys Gln Gly
            260                 265                 270 ctc tgc tgt tcc ttc tgc aag tac aca gtc cat gag cgc tgt gtg gct        864
Leu Cys Cys Ser Phe Cys Lys Tyr Thr Val His Glu Arg Cys Val Ala
        275                 280                 285 cga gca cct ccc tct tgc atc aag acc tat gtg aag tcc aaa agg aac        912
Arg Ala Pro Pro Ser Cys Ile Lys Thr Tyr Val Lys Ser Lys Arg Asn
    290                 295                 300 act gat gtc atg cac cat tac tgg gtt gaa ggt aac tgc cca acc aag        960
Thr Asp Val Met His His Tyr Trp Val Glu Gly Asn Cys Pro Thr Lys
305                 310                 315                 320 tgt gat aag tgc cac aaa act gtt aaa tgt tac cag ggc ctg aca gga       1008
Cys Asp Lys Cys His Lys Thr Val Lys Cys Tyr Gln Gly Leu Thr Gly
                325                 330                 335 ctg cat tgt gtt tgg tgt cag atc aca ctg cat aat aaa tgt gct tct       1056
Leu His Cys Val Trp Cys Gln Ile Thr Leu His Asn Lys Cys Ala Ser
            340                 345                 350 cat cta aaa cct gaa tgt gac tgt gga cct ttg aag gac cat att tta       1104
His Leu Lys Pro Glu Cys Asp Cys Gly Pro Leu Lys Asp His Ile Leu
        355                 360                 365 cca ccc aca aca atc tgt cca gtg gta ctg cag act ctg ccc act tca       1152
Pro Pro Thr Thr Ile Cys Pro Val Val Leu Gln Thr Leu Pro Thr Ser
    370                 375                 380 gga gtt tca gtt cct gag gaa aga caa tca aca gtg aaa aag gaa aag       1200
Gly Val Ser Val Pro Glu Glu Arg Gln Ser Thr Val Lys Lys Glu Lys
385                 390                 395                 400 agt ggt tcc cag cag cca aac aaa gtg att gac aag aat aaa atg caa       1248
Ser Gly Ser Gln Gln Pro Asn Lys Val Ile Asp Lys Asn Lys Met Gln
                405                 410                 415 aga gcc aac tct gtt act gta gat gga caa ggc ctg cag gtc act cct       1296
Arg Ala Asn Ser Val Thr Val Asp Gly Gln Gly Leu Gln Val Thr Pro
            420                 425                 430 gtg cct ggt act cac cca ctt tta gtt ttt gtg aac ccc aaa agt ggt       1344
Val Pro Gly Thr His Pro Leu Leu Val Phe Val Asn Pro Lys Ser Gly
        435                 440                 445
```

-continued

```
gga aaa caa gga gaa cga att tac aga aaa ttc cag tat cta tta aat      1392
Gly Lys Gln Gly Glu Arg Ile Tyr Arg Lys Phe Gln Tyr Leu Leu Asn
    450                 455                 460 cct cgt cag gtt tac agt ctt tct gga aat gga cca atg cca ggg tta      1440
Pro Arg Gln Val Tyr Ser Leu Ser Gly Asn Gly Pro Met Pro Gly Leu
465                 470                 475                 480 aac ttt ttc cgt gat gtt cct gac ttc aga gtg tta gcc tgt ggt gga      1488
Asn Phe Phe Arg Asp Val Pro Asp Phe Arg Val Leu Ala Cys Gly Gly
                485                 490                 495 gat gga acc gtg ggc tgg gtt ttg gat tgc ata gaa aag gcc aat gta      1536
Asp Gly Thr Val Gly Trp Val Leu Asp Cys Ile Glu Lys Ala Asn Val
        500                 505                 510 ggc aag cat cct cca gtt gcg att ctg cct ctt ggg act ggc aat gat      1584
Gly Lys His Pro Pro Val Ala Ile Leu Pro Leu Gly Thr Gly Asn Asp
            515                 520                 525 cta gca aga tgc ctg cga tgg gga gga ggt tac gaa ggt gag aat ctg      1632
Leu Ala Arg Cys Leu Arg Trp Gly Gly Gly Tyr Glu Gly Glu Asn Leu
    530                 535                 540 atg aaa att cta aaa gac att gaa aac agc aca gaa atc atg ttg gac      1680
Met Lys Ile Leu Lys Asp Ile Glu Asn Ser Thr Glu Ile Met Leu Asp
545                 550                 555                 560 agg tgg aag ttt gaa gtc ata cct aat gac aaa gat gag aaa gga gac      1728
Arg Trp Lys Phe Glu Val Ile Pro Asn Asp Lys Asp Glu Lys Gly Asp
                565                 570                 575 cca gtg cct tac agt atc atc aat aat tac ttt tcc att ggc gtg gat      1776
Pro Val Pro Tyr Ser Ile Ile Asn Asn Tyr Phe Ser Ile Gly Val Asp
        580                 585                 590 gcc tcc att gca cac aga ttc cac atc atg aga gaa aaa cac cca gag      1824
Ala Ser Ile Ala His Arg Phe His Ile Met Arg Glu Lys His Pro Glu
            595                 600                 605 aaa ttc aac agt aga atg aag aac aaa ttt tgg tat ttt gag ttt ggc      1872
Lys Phe Asn Ser Arg Met Lys Asn Lys Phe Trp Tyr Phe Glu Phe Gly
    610                 615                 620 aca tct gaa act ttc tca gcc acc tgc aag aag cta cat gaa tct gta      1920
Thr Ser Glu Thr Phe Ser Ala Thr Cys Lys Lys Leu His Glu Ser Val
625                 630                 635                 640 gaa ata gaa tgt gat gga gta cag ata gat tta ata aac atc tct ctg      1968
Glu Ile Glu Cys Asp Gly Val Gln Ile Asp Leu Ile Asn Ile Ser Leu
                645                 650                 655 gaa gga att gct att ttg aat ata cca agc atg cat gga gga tcc aat      2016
Glu Gly Ile Ala Ile Leu Asn Ile Pro Ser Met His Gly Gly Ser Asn
        660                 665                 670 ctt tgg gga gag tct aag aaa aga cga agc cat cga cga ata gag aaa      2064
Leu Trp Gly Glu Ser Lys Lys Arg Arg Ser His Arg Arg Ile Glu Lys
            675                 680                 685 aaa ggg tct gac aaa agg acc acc gtc aca gat gcc aaa gag ttg aag      2112
Lys Gly Ser Asp Lys Arg Thr Thr Val Thr Asp Ala Lys Glu Leu Lys
    690                 695                 700 ttt gca agt caa gat ctc agt gac cag ctg ctg gag gtg gtc ggc ttg      2160
Phe Ala Ser Gln Asp Leu Ser Asp Gln Leu Leu Glu Val Val Gly Leu
705                 710                 715                 720 gaa gga gcc atg gag atg ggg caa ata tac aca ggc ctg aaa agt gct      2208
Glu Gly Ala Met Glu Met Gly Gln Ile Tyr Thr Gly Leu Lys Ser Ala
                725                 730                 735 ggc cgg cgg ctg gct cag tgc tcc tgc gtg gtc atc agg acg agc aag      2256
Gly Arg Arg Leu Ala Gln Cys Ser Cys Val Val Ile Arg Thr Ser Lys
        740                 745                 750 tct ctg cca atg caa att gat ggg gag cca tgg atg cag acc cca tgc      2304
Ser Leu Pro Met Gln Ile Asp Gly Glu Pro Trp Met Gln Thr Pro Cys
    755                 760                 765
```

-continued

```
aca gtg agt aca gag tag ttgatatgct atgtcaatct cagttttgct        2352
Thr Val Ser Thr Glu
    770 ttcctctttg actaaataac cacaataact gattttttc tttatttctt ttcaacctat  2412 cagcaaatag tcttttttgtt gttgttgtta tgtgtgtgtc agagccacta catttaggct 2472 gtagacatta tataccctttg gcaatgattt agctcttgaa tgtttgtgct agcctaagta 2532 taaatagatc ttttaaatag atcaattata aaccatagat caattataaa ctatggagct 2592 aaacaaaata ttaataaaag tttatctgaa actttttttgt ttatttcaga gcacattatt 2652 agaatattat ttgcgagaaa tgcagaccta agcttatatg tgaacttatt tctcagcttt  2712 tctatgcctc catttgggga tttgagggct ttcttctcca taagaaaaaa atttctctcc  2772 agtttctacc ataattaatt gtgttttcca gaatgaggta ttatttaagg cagacactgc  2832 ccctctcaaa aaaatcagt tttcatttgc atagtgaata ttttattgca tttcaaaaac   2892 atgctaggaa ctgcttttgg cactgggagt agacacatga acaagaccaa cagtgtaatt  2952 tccttcaagt tacttacatt cctataatag aggaccgaat aaataaacaa ctacatgata  3012 aatataactt cagactgtga gagttattaa aaaataaggt gaaatgatga taagaagctg  3072 gattaggtgt ggagaataaa tactacttga gataagggag acctctttga aaggacatag  3132 ccaaaagctt agtataaaat taaaaaaaat aaaaaaaaaa                       3172
```

<210> SEQ ID NO 5
<211> LENGTH: 773
<212> TYPE: PRT
<213> ORGANISM: Homo sapiens

<400> SEQUENCE: 5

```
Met Thr Asn Gln Glu Lys Trp Ala His Leu Ser Pro Ser Glu Phe Ser
  1               5                  10                  15

Gln Leu Gln Lys Tyr Ala Glu Tyr Ser Thr Lys Lys Leu Lys Asp Val
             20                  25                  30

Leu Glu Glu Phe His Gly Asn Gly Val Leu Ala Lys Tyr Asn Pro Glu
         35                  40                  45

Gly Lys Gln Asp Ile Leu Asn Gln Thr Ile Asp Phe Glu Gly Phe Lys
     50                  55                  60

Leu Phe Met Lys Thr Phe Leu Glu Ala Glu Leu Pro Asp Asp Phe Thr
 65                  70                  75                  80

Ala His Leu Phe Met Ser Phe Ser Asn Lys Phe Pro His Ser Ser Pro
                 85                  90                  95

Met Val Lys Ser Lys Pro Ala Leu Leu Ser Gly Gly Leu Arg Met Asn
            100                 105                 110

Lys Gly Ala Ile Thr Pro Pro Arg Thr Thr Ser Pro Ala Asn Thr Cys
        115                 120                 125

Ser Pro Glu Val Ile His Leu Lys Asp Ile Val Cys Tyr Leu Ser Leu
    130                 135                 140

Leu Glu Arg Gly Arg Pro Glu Asp Lys Leu Glu Phe Met Phe Arg Leu
145                 150                 155                 160

Tyr Asp Thr Asp Gly Asn Gly Phe Leu Asp Ser Ser Glu Leu Glu Asn
                165                 170                 175

Ile Ile Ser Gln Met Met His Val Ala Glu Tyr Leu Glu Trp Asp Val
            180                 185                 190

Thr Glu Leu Asn Pro Ile Leu His Glu Met Met Glu Glu Ile Asp Tyr
        195                 200                 205
```

```
Asp His Asp Gly Thr Val Ser Leu Glu Glu Trp Ile Gln Gly Gly Met
210                 215                 220

Thr Thr Ile Pro Leu Leu Val Leu Leu Gly Leu Glu Asn Asn Val Lys
225                 230                 235                 240

Asp Asp Gly Gln His Val Trp Arg Leu Lys His Phe Asn Lys Pro Ala
                245                 250                 255

Tyr Cys Asn Leu Cys Leu Asn Met Leu Ile Gly Val Gly Lys Gln Gly
                260                 265                 270

Leu Cys Cys Ser Phe Cys Lys Tyr Thr Val His Glu Arg Cys Val Ala
            275                 280                 285

Arg Ala Pro Pro Ser Cys Ile Lys Thr Tyr Val Lys Ser Lys Arg Asn
290                 295                 300

Thr Asp Val Met His His Tyr Trp Val Glu Gly Asn Cys Pro Thr Lys
305                 310                 315                 320

Cys Asp Lys Cys His Lys Thr Val Lys Cys Tyr Gln Gly Leu Thr Gly
                325                 330                 335

Leu His Cys Val Trp Cys Gln Ile Thr Leu His Asn Lys Cys Ala Ser
                340                 345                 350

His Leu Lys Pro Glu Cys Asp Cys Gly Pro Leu Lys Asp His Ile Leu
            355                 360                 365

Pro Pro Thr Thr Ile Cys Pro Val Leu Gln Thr Leu Pro Thr Ser
370                 375                 380

Gly Val Ser Val Pro Glu Glu Arg Gln Ser Thr Val Lys Lys Glu Lys
385                 390                 395                 400

Ser Gly Ser Gln Gln Pro Asn Lys Val Ile Asp Lys Asn Lys Met Gln
                405                 410                 415

Arg Ala Asn Ser Val Thr Val Asp Gly Gln Gly Leu Gln Val Thr Pro
                420                 425                 430

Val Pro Gly Thr His Pro Leu Leu Val Phe Val Asn Pro Lys Ser Gly
            435                 440                 445

Gly Lys Gln Gly Glu Arg Ile Tyr Arg Lys Phe Gln Tyr Leu Leu Asn
450                 455                 460

Pro Arg Gln Val Tyr Ser Leu Ser Gly Asn Gly Pro Met Pro Gly Leu
465                 470                 475                 480

Asn Phe Phe Arg Asp Val Pro Asp Phe Arg Val Leu Ala Cys Gly Gly
                485                 490                 495

Asp Gly Thr Val Gly Trp Val Leu Asp Cys Ile Glu Lys Ala Asn Val
                500                 505                 510

Gly Lys His Pro Pro Val Ala Ile Leu Pro Leu Gly Thr Gly Asn Asp
            515                 520                 525

Leu Ala Arg Cys Leu Arg Trp Gly Gly Gly Tyr Glu Gly Glu Asn Leu
530                 535                 540

Met Lys Ile Leu Lys Asp Ile Glu Asn Ser Thr Glu Ile Met Leu Asp
545                 550                 555                 560

Arg Trp Lys Phe Glu Val Ile Pro Asn Asp Lys Asp Glu Lys Gly Asp
                565                 570                 575

Pro Val Pro Tyr Ser Ile Ile Asn Asn Tyr Phe Ser Ile Gly Val Asp
                580                 585                 590

Ala Ser Ile Ala His Arg Phe His Ile Met Arg Glu Lys His Pro Glu
            595                 600                 605

Lys Phe Asn Ser Arg Met Lys Asn Lys Phe Trp Tyr Phe Glu Phe Gly
610                 615                 620
```

-continued

```
Thr Ser Glu Thr Phe Ser Ala Thr Cys Lys Lys Leu His Glu Ser Val
625                 630                 635                 640

Glu Ile Glu Cys Asp Gly Val Gln Ile Asp Leu Ile Asn Ile Ser Leu
            645                 650                 655

Glu Gly Ile Ala Ile Leu Asn Ile Pro Ser Met His Gly Gly Ser Asn
                660                 665                 670

Leu Trp Gly Glu Ser Lys Lys Arg Arg Ser His Arg Ile Glu Lys
            675                 680                 685

Lys Gly Ser Asp Lys Arg Thr Thr Val Thr Asp Ala Lys Glu Leu Lys
    690                 695                 700

Phe Ala Ser Gln Asp Leu Ser Asp Gln Leu Leu Glu Val Val Gly Leu
705                 710                 715                 720

Glu Gly Ala Met Glu Met Gly Gln Ile Tyr Thr Gly Leu Lys Ser Ala
                725                 730                 735

Gly Arg Arg Leu Ala Gln Cys Ser Cys Val Val Ile Arg Thr Ser Lys
            740                 745                 750

Ser Leu Pro Met Gln Ile Asp Gly Glu Pro Trp Met Gln Thr Pro Cys
        755                 760                 765

Thr Val Ser Thr Glu
        770
```

<210> SEQ ID NO 6
<211> LENGTH: 3172
<212> TYPE: DNA
<213> ORGANISM: Homo sapiens

<400> SEQUENCE: 6

| | | | | |
|---|---|---|---|---|
| tttttttttt | atttttttta | attttatact | aagcttttgg | ctatgtcctt | tcaaagaggt | 60 |
| ctcccttatc | tcaagtagta | tttattctcc | acacctaatc | cagcttctta | tcatcatttc | 120 |
| accttatttt | ttaataactc | tcacagtctg | aagttatatt | tatcatgtag | ttgtttattt | 180 |
| attcggtcct | ctattatagg | aatgtaagta | acttgaagga | aattacactg | ttggtcttgt | 240 |
| tcatgtgtct | actcccagtg | ccaaaagcag | ttcctagcat | gttttttgaaa | tgcaataaaa | 300 |
| tattcactat | gcaaatgaaa | actgattttt | tttgagaggg | gcagtgtctg | ccttaaataa | 360 |
| tacctcattc | tggaaaacac | aattaattat | ggtagaaact | ggagagaaat | ttttttctta | 420 |
| tggagaagaa | agccctcaaa | tccccaaatg | gaggcataga | aaagctgaga | aataagttca | 480 |
| catataagct | taggtctgca | tttctcgcaa | ataatattct | aataatgtgc | tctgaaataa | 540 |
| acaaaaaagt | ttcagataaa | cttttattaa | tattttgttt | agctccatag | tttataattg | 600 |
| atctatggtt | tataattgat | ctatttaaaa | gatctattta | tacttaggct | agcacaaaca | 660 |
| ttcaagagct | aaatcattgc | caagggtata | taatgtctac | agcctaaatg | tagtggctct | 720 |
| gacacacaca | taacaacaac | aacaaaaaga | ctatttgctg | ataggttgaa | aagaaataaa | 780 |
| gaaaaaaatc | agttattgtg | gttatttagt | caaagaggaa | agcaaaactg | agattgacat | 840 |
| agcatatcaa | ctactctgta | ctcactgtgc | atgggtctg | catccatggc | tccccatcaa | 900 |
| tttgcattgg | cagagacttg | ctcgtcctga | tgaccacgca | ggagcactga | gccagccgcc | 960 |
| ggccagcact | tttcaggcct | gtgtatattt | gccccatctc | catggctcct | tccaagccga | 1020 |
| ccacctccag | cagctggtca | ctgagatctt | gacttgcaaa | cttcaactct | ttggcatctg | 1080 |
| tgacggtggt | cctttttgtca | gaccttttt | tctctattcg | tcgatggctt | cgtcttttct | 1140 |
| tagactctcc | ccaaagattg | gatcctccat | gcatgcttgg | tatattcaaa | atagcaattc | 1200 |
| cttccagaga | gatgtttatt | aaatctatct | gtactccatc | acattctatt | tctacagatt | 1260 |

-continued

```
catgtagctt cttgcaggtg gctgagaaag tttcagatgt gccaaactca aaataccaaa    1320
atttgttctt cattctactg ttgaatttct ctgggtgttt ttctctcatg atgtggaatc    1380
tgtgtgcaat ggaggcatcc acgccaatgg aaaagtaatt attgatgata ctgtaaggca    1440
ctgggtctcc tttctcatct ttgtcattag gtatgacttc aaacttccac ctgtccaaca    1500
tgatttctgt gctgttttca atgtctttta gaattttcat cagattctca ccttcgtaac    1560
ctcctcccca tcgcaggcat cttgctagat cattgccagt cccaagaggc agaatcgcaa    1620
ctggaggatg cttgcctaca ttggccttttt ctatgcaatc aaaacccag cccacggttc    1680 catctccacc acaggctaac actctgaagt caggaacatc acggaaaaag tttaaccctg    1740
gcattggtcc atttccagaa agactgtaaa cctgacgagg atttaataga tactggaatt    1800
ttctgtaaat tcgttctcct tgttttccac cacttttggg gttcacaaaa actaaaagtg    1860
ggtgagtacc aggcacagga gtgacctgca ggccttgtcc atctacagta acagagttgg    1920
ctctttgcat tttattcttg tcaatcactt tgtttggctg ctgggaacca ctcttttcct    1980
ttttcactgt tgattgtctt tcctcaggaa ctgaaactcc tgaagtgggc agagtctgca    2040
gtaccactgg acagattgtt gtgggtggta aaatatggtc cttcaaaggt ccacagtcac    2100
attcaggttt tagatgagaa gcacatttat tatgcagtgt gatctgacac caaacacaat    2160
gcagtcctgt caggccctgg taacattttaa cagttttgtg gcacttatca cacttggttg    2220
ggcagttacc ttcaacccag taatggtgca tgacatcagt gttccttttg gacttccacat    2280 aggtcttgat gcaagaggga ggtgctcgag ccacacagcg ctcatggact gtgtacttgc    2340
agaaggaaca gcagaggccc tgcttcccca cgccaatcag catgttcagg caaaggttgc    2400
aataggcagg tttgttaaag tgcttcagtc gccacacgtg ctgtccatca tccttcacgt    2460 tatttttctaa gcccaggagc acaagaagtg gaatcgttgt cattcctcct tgaatccatt    2520
cctccagaga cacggttcca tcatgatcat agtcaatttc ttccatcatt tcatggagga    2580
ttggattaag ttcagtgaca tcccactcaa ggtattctgc aacatgcatc atctgactga    2640
tgatattttc tagctccgag ctgtccagga agccattccc atccgtgtca taaaggcgaa    2700
acataaactc aagcttatcc tcaggtcttc ctctttcaag cagagacagg taacagacaa    2760
tgtccttcag atggattact tctggggaac acgtatttgc aggagaagta gttcggggag    2820
gggtgatggc acctttattc attctcgac cgcctgatag gagagcaggc ttactttta    2880 ccattggact agaatgagga aacttgttgc taaatgacat gaaaaggtgt gcagtgaaat    2940
catcaggaag ctcggcttcc aggaatgtct tcatgaatag tttgaaacct tcaaaatcta    3000
ttgtttggtt aagaatgtct tgtttccctt caggattata ctttgcaagc acaccattac    3060
catggaattc ttcaagaaca tcctttaatt tctttgtaga atactcagca tatttctgaa    3120
gttgggaaaa ttccgaaggg ctgaggtggg cccattttc ctggtttgtc at           3172
```

<210> SEQ ID NO 7
<211> LENGTH: 801
<212> TYPE: PRT
<213> ORGANISM: Rattus sp.

<400> SEQUENCE: 7

Met Thr Asn Gln Glu Lys Trp Ala His Leu Ser Pro Ser Glu Phe Ser
 1               5                  10                  15

Gln Leu Gln Lys Tyr Ala Glu Tyr Ser Thr Lys Lys Leu Lys Asp Val
                20                  25                  30

```
Leu Glu Glu Phe His Gly Asn Gly Val Leu Ala Lys Tyr Asn Pro Glu
         35                  40                  45

Gly Lys Gln Asp Ile Leu Asn Gln Thr Ile Asp Phe Glu Gly Phe Lys
         50                  55                  60

Leu Phe Met Lys Thr Phe Leu Glu Ala Glu Leu Pro Asp Asp Phe Thr
 65                  70                  75                  80

Ala His Leu Phe Met Ser Phe Ser Asn Lys Phe Pro His Ser Ser Pro
                 85                  90                  95

Asn Val Lys Ser Lys Pro Ala Leu Leu Ser Gly Gly Leu Arg Met Asn
             100                 105                 110

Lys Gly Ala Ile Thr Pro Pro Arg Ser Ser Pro Ala Asn Thr Cys Phe
             115                 120                 125

Pro Glu Val Ile His Leu Lys Asp Ile Val Cys Tyr Leu Ser Leu Leu
         130                 135                 140

Glu Arg Gly Arg Pro Glu Asp Lys Leu Glu Phe Met Phe Arg Leu Tyr
145                 150                 155                 160

Asp Thr Asp Gly Asn Gly Phe Leu Asp Ser Ser Glu Leu Glu Asn Ile
                 165                 170                 175

Ile Gly Gln Met Met His Val Ala Glu Tyr Leu Glu Trp Asp Val Thr
             180                 185                 190

Glu Leu Asn Pro Ile Leu His Glu Met Met Glu Ile Asp Tyr Asp
         195                 200                 205

Arg Asp Gly Thr Val Ser Leu Glu Glu Trp Ile Gln Gly Met Thr
210                 215                 220

Thr Ile Pro Leu Leu Val Leu Gly Leu Glu Asn Asn Val Lys Asp
225                 230                 235                 240

Asp Gly Gln His Val Trp Arg Leu Lys His Phe Asn Lys Pro Ala Tyr
             245                 250                 255

Cys Asn Leu Cys Leu Asn Met Leu Ile Gly Val Gly Lys Gln Gly Leu
             260                 265                 270

Cys Cys Ser Phe Cys Lys Tyr Thr Val His Glu Arg Cys Ala Arg Ala
         275                 280                 285

Pro Pro Ser Cys Ile Lys Thr Tyr Val Lys Ser Lys Asn Thr Asp
         290                 295                 300

Val Met His His Tyr Trp Val Glu Gly Asn Cys Pro Thr Lys Cys Asp
305                 310                 315                 320

Lys Cys His Lys Thr Val Lys Cys Tyr Gln Gly Leu Thr Gly Leu His
             325                 330                 335

Cys Val Trp Cys Gln Thr Thr Leu His Asn Lys Cys Ala Ser His Leu
             340                 345                 350

Lys Pro Glu Cys Asp Cys Gly Pro Leu Lys Asp His Ile Leu Pro Pro
         355                 360                 365

Thr Thr Ile Cys Pro Val Val Leu Thr Met Pro Thr Ala Gly Thr Ser
         370                 375                 380

Val Pro Glu Glu Arg Gln Ser Thr Ala Lys Lys Glu Lys Gly Ser Ser
385                 390                 395                 400

Gln Gln Pro Asn Lys Val Thr Asp Lys Asn Lys Met Gln Arg Ala Asn
             405                 410                 415

Ser Val Thr Met Asp Gly Gln Leu Gln Ile Thr Pro Ile Pro Gly
             420                 425                 430

Thr His Pro Leu Leu Val Phe Val Asn Pro Lys Ser Gly Gly Lys Gln
         435                 440                 445

Gly Glu Arg Ile Tyr Arg Lys Phe Gln Tyr Leu Leu Asn Pro Arg Gln
```

-continued

```
            450                 455                 460
Val Tyr Ser Leu Ser Gly Asn Gly Pro Met Pro Gly Leu His Phe Phe
465                 470                 475                 480

Arg Asp Val Pro Asp Phe Arg Val Leu Ala Cys Gly Gly Asp Gly Thr
                485                 490                 495

Val Gly Trp Ile Leu Asp Cys Ile Glu Lys Ala Asn Val Val Lys His
                500                 505                 510

Pro Pro Val Ala Ile Leu Pro Leu Gly Thr Gly Asn Asp Leu Ala Arg
            515                 520                 525

Cys Leu Arg Trp Gly Gly Tyr Glu Gly Glu Asn Leu Met Lys Ile
            530                 535                 540

Leu Lys Asp Ile Glu Ser Ser Thr Glu Ile Met Leu Asp Arg Trp Lys
545                 550                 555                 560

Phe Glu Val Thr Pro Asn Asp Lys Asp Glu Lys Gly Asp Pro Val Pro
                565                 570                 575

Tyr Ser Ile Ile Asn Asn Tyr Phe Ser Ile Gly Val Asp Ala Ser Ile
                580                 585                 590

Ala His Arg Phe His Ile Met Arg Glu Lys His Pro Glu Lys Phe Asn
            595                 600                 605

Ser Arg Met Lys Asn Lys Phe Trp Tyr Phe Glu Phe Gly Thr Ser Glu
            610                 615                 620

Thr Phe Ser Ala Thr Cys Lys Lys Leu His Glu Ser Val Glu Ile Glu
625                 630                 635                 640

Cys Asp Gly Val Gln Ile Asp Leu Ile Asn Ile Ser Leu Gln Gly Ile
                645                 650                 655

Ala Ile Leu Asn Ile Pro Ser Met His Gly Gly Ser Asn Leu Trp Gly
                660                 665                 670

Glu Ser Lys Lys Lys Arg Ser His Arg Arg Ile Glu Lys Lys Gly Ser
            675                 680                 685

Asp Lys Arg Pro Thr Leu Thr Asp Ala Lys Glu Leu Lys Phe Ala Ser
            690                 695                 700

Gln Asp Leu Ser Asp Gln Leu Leu Glu Val Val Gly Leu Glu Gly Ala
705                 710                 715                 720

Met Glu Met Gly Gln Ile Tyr Thr Gly Leu Lys Ser Ala Gly Arg Arg
                725                 730                 735

Leu Ala Gln Cys Ser Ser Val Val Ile Arg Thr Ser Lys Ser Leu Pro
                740                 745                 750

Met Gln Ile Asp Gly Glu Pro Trp Met Gln Thr Pro Cys Thr Ile Lys
            755                 760                 765

Ile Thr His Lys Asn Gln Ala Pro Met Leu Met Gly Pro Pro Lys
            770                 775                 780

Thr Gly Leu Phe Cys Ser Leu Ile Lys Arg Thr Arg Asn Arg Ser Lys
785                 790                 795                 800

Glu
```